US011441194B2

(12) United States Patent
Bastian et al.

(10) Patent No.: US 11,441,194 B2
(45) Date of Patent: Sep. 13, 2022

(54) METHODS AND PROBE COMBINATIONS FOR DETECTING MELANOMA

(71) Applicants: ABBOTT MOLECULAR INC., Des Plaines, IL (US); The Regents of the University of California, Oakland, CA (US)

(72) Inventors: Boris Bastian, Mill Valley, CA (US); Larry E. Morrison, Oro Valley, AZ (US); Susan Jewell, Elmhurst, IL (US)

(73) Assignees: Abbott Molecular Inc., Des Plaines, IL (US); The Regents of the University of California, Oakland, CA (US)

( * ) Notice: Subject to any disclaimer, the term of this patent is extended or adjusted under 35 U.S.C. 154(b) by 54 days.

(21) Appl. No.: 17/146,366

(22) Filed: Jan. 11, 2021

(65) Prior Publication Data

US 2021/0238692 A1   Aug. 5, 2021

Related U.S. Application Data

(63) Continuation of application No. 11/515,505, filed on Sep. 1, 2006, now abandoned.

(60) Provisional application No. 60/713,799, filed on Sep. 2, 2005.

(51) Int. Cl.
*C12Q 1/6886* (2018.01)
*C12Q 1/6841* (2018.01)

(52) U.S. Cl.
CPC ......... *C12Q 1/6886* (2013.01); *C12Q 1/6841* (2013.01); *C12Q 2537/143* (2013.01); *C12Q 2600/112* (2013.01); *C12Q 2600/158* (2013.01)

(58) Field of Classification Search
None
See application file for complete search history.

(56) References Cited

U.S. PATENT DOCUMENTS

| | | |
|---|---|---|
| 2001/0038833 A1 | 11/2001 | Rybak et al. |
| 2003/0073119 A1 | 4/2003 | Bastian et al. |
| 2005/0026190 A1 | 2/2005 | Sokolova et al. |
| 2006/0211019 A1 | 9/2006 | Hailing et al. |
| 2007/0059747 A1 | 3/2007 | Bastian et al. |
| 2011/0300540 A1 | 12/2011 | Bastian et al. |

FOREIGN PATENT DOCUMENTS

| | | |
|---|---|---|
| EP | 1035215 | 9/2000 |
| WO | WO 2000/061814 | 10/2000 |
| WO | WO 2002/066685 | 8/2002 |
| WO | WO 2007/028031 | 3/2007 |

OTHER PUBLICATIONS

Abdel-Rahman et al. (2005) "Expression of Vascular Endothelial Growth Factor in Uveal Melanoma Is Independent of 6p21-Region Copy Number," *Clin Cancer Res*, 11:73-78.

Balazs et al. (2001) "Chromosomal imbalances in primary and metastatic melanomas revealed by comparative genomic hybridization," *Cytometry*, 46(4):222-232.

Barghorn et al. (Jun. 2001) "Putative Tumor Suppressor Loci at 6q22 and 6q23-q24 Are Involved in the Malignant Progression of Sporadic Endocrine Pancreatic Tumors" *American Journal of Pathology*, 158(6):1903-1911.

Bastian et al. (1998) "Chromosomal Gains and Losses in Primary Cutaneous Melanomas Detected by Comparative Genomic Hybridization," *Cancer Research*, 58:2170-2175.

Bastian et al. (2000) "Gene Amplifications Characterize Acral Melanoma and Permit the Detection of Occult Tumor Cells in the Surrounding Skin," *Cancer Research*, 60:1968-1973.

Bastian et al. (2001) "Genomic Approaches to Skin Cancer Diagnosis," *Arch Dermatol*, 137:1507-1511.

Bastian et al. (2003) "Classifying Melanocytic Tumors Based on DNA Copy Number Changes," *American Journal of Pathology*, 163(5):1765-1770.

Blixt et al. (1998) "The Two-Exon Gene of the Human Forkhead Transcription Factor FREAC-2 (FKHL6) Is Located at 6p25.3," *Genomics*, 53:387-390.

Casorzo et al. (2005) "Fluorescence in situ hybridization (FISH) evaluation of chromosomes 6, 7, 9 and 10 throughout human melanocytic tumorigenesis," *Melanoma Research*, 15(3):155-160.

Davies et al. (1999) "An interstitial deletion of 6p24-p25 proximal to the FKHL7 locus and including AP-2á that affects anterior eye chamber development." *Journal of Medical Genetics*, 36:708-710.

Dunham et al. (1992) "Rapid generation of chromosome-specific alphoid DNA probes using the polymerase chain reaction" *Human Genetics*, 88:457-462.

Franke et al. (2001) "Lymphocyte predominance Hodgkin disease is characterized by recurrent genomic imbalances," *Blood*, 97(6):1845-1853.

Healy et al. (Feb. 1, 1996) "Allelotypes of Primary Cutaneous Melanoma and Benign Melanocytic Nevi," *Cancer Research*, 56:589-593.

Hughes et al. (2005) "Microarray comparative genomic hybridisation analysis of intraocular uveal melanomas identifies distinctive imbalances associated with loss of chromosome 3," *British Journal of Cancer*, 93:1191-1196.

Katz et al. (2000) "Detection of Chromosome 11q13 Breakpoints by Interphase Fluorescence In Situ Hybridization" *American Journal of Clinical Pathology*, 114:248-257.

Lindqvist et al. (2000) "A Susceptibility Locus for Human Systemic Lupus Erythematosus (hSLE1) on Chromosome 2q," *Journal of Autoimmunity*, 14:169-178.

Lublin et al. (Jul. 1, 1988) "Molecular Cloning and Chromosomal Localization of Human Membrane Cofactor Protein (MCP)" *Journal of Experimental Medicine*, 168(1):181-194.

Matsuta et al. (1997) "Detection of numerical chromosomal aberrations in malignant melanomas using fluorescence in situ hybridization," *Journal of Cutaneous Pathology*, 24(4):201-205.

(Continued)

*Primary Examiner* — Katherine D Salmon
(74) *Attorney, Agent, or Firm* — Emily M. Haliday; Weaver Austin Villeneuve & Sampson LLP

(57) ABSTRACT

The present invention is based on the discovery of methods and combinations of probes to chromosomal regions that are gained or lost or imbalanced in melanoma that provide highly specific and sensitive assays for the detection of melanoma cells.

9 Claims, 6 Drawing Sheets

(56) References Cited

OTHER PUBLICATIONS

Millikin et al. (1991) "Loss of Heterozygosity for Loci on the Long Arm of Chromosome 6 in Human Malignant Melanoma," *Cancer Research*, 51:5449-5453.

Namiki et al. (2005) "Genomic alterations in primary cutaneous melanomas detected by metaphase comparative genomic hybridization with laser capture or manual microdissection: 6p gains may predict poor outcome," *Cancer Genetics and Cytogenetics*, 157(1): 1-11.

Naus et al. (2001) "Characterization of Complex Chromosomal Abnormalities in Uveal Melanoma by Fluorescence In Situ Hybridization, Spectral Karyotyping, and Comparative Genomic Hybridization," *Genes, Chromosomes & Cancer*, 30:267-273.

Patel et al. (2001) "Prediction of prognosis in patients with uveal melanoma using fluorescence in situ hybridisation," *British Journal of Ophthalmology*, 85(12):1440-1444.

Robertson et al. (1996) "Mechanisms of Human Melanoma Cell Growth and Tumor Suppression by Chromosome 6," *Cancer Res*, 56:1635-1641.

Sokolova et al. (2002) "A Fluorescence In Situ Hybridization-Based Assay for Improved Detection of Lung Cancer Cells in Bronchial Washing Specimens" *Cancer Cytopathology*, 96: 306-315.

Smith et al. (Feb. 1988) "Clinical and Biologic Characterization of T-Cell Neoplasias With Rearrangements of Chromosome 7 Band q34" *Blood*, 71(2):395-402.

Tanner et al. (Dec. 1995) "Amplification of Chromosomal Region 20q13 in Invasive Breast Cancer: Prognostic Implications" *Clinical Cancer Research*, 1(12):1455-1461.

Tschentscher et al. (2000) "Identification of chromosomes 3, 6, and 8 aberrations in uveal melanoma by microsatellite analysis in comparison to comparative genomic hybridization," *Cancer Genetics and Cytogenetics*, 122:13-17.

Varanasi et al. (Apr. 12, 1994) "Isolation of the human peroxisomal acyl-CoA oxidase gene:Organization, promoter analysis, and chromosomal localization" *Proceedings of the National Academy of Sciences USA*, 91(8):3107-3111.

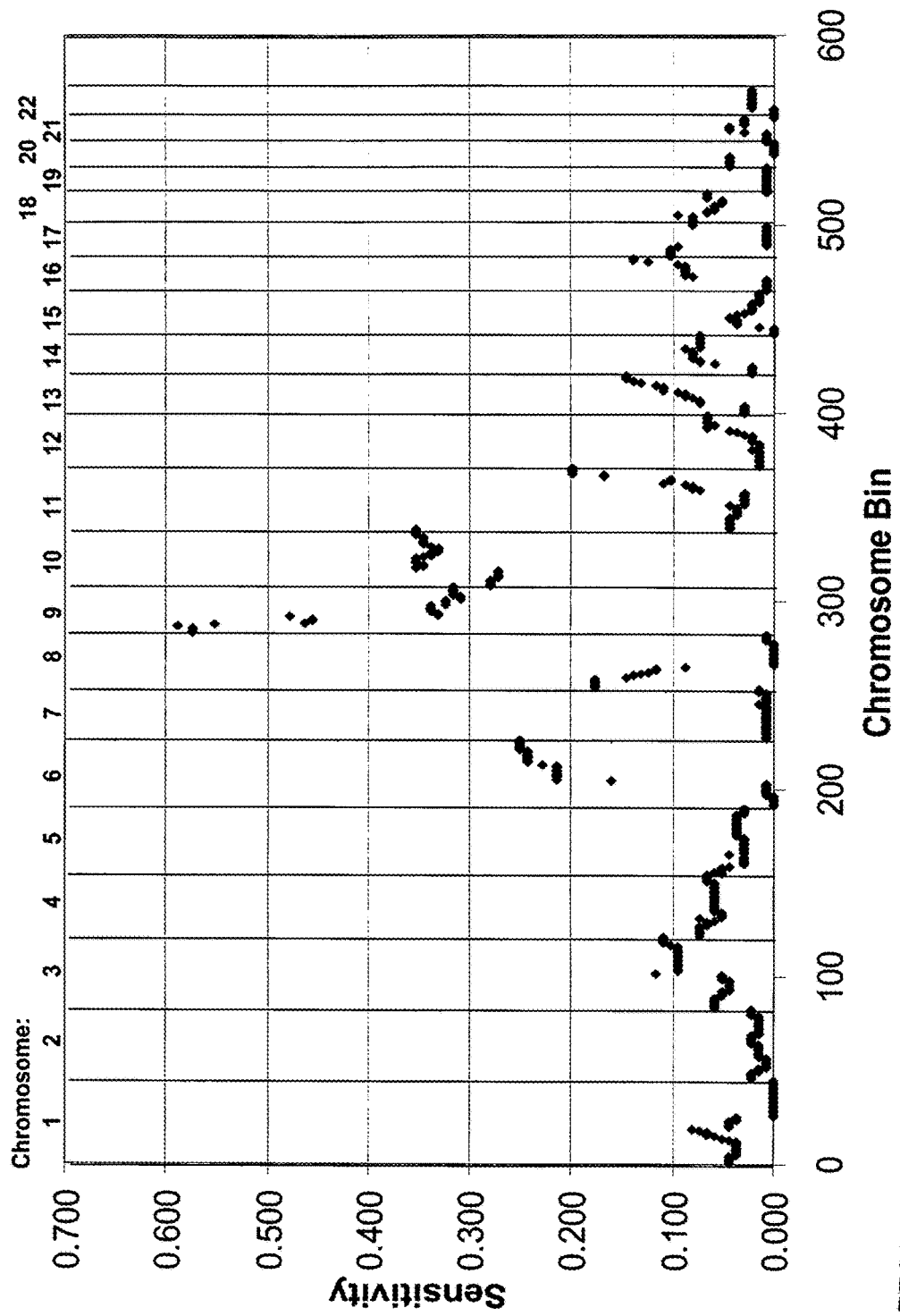

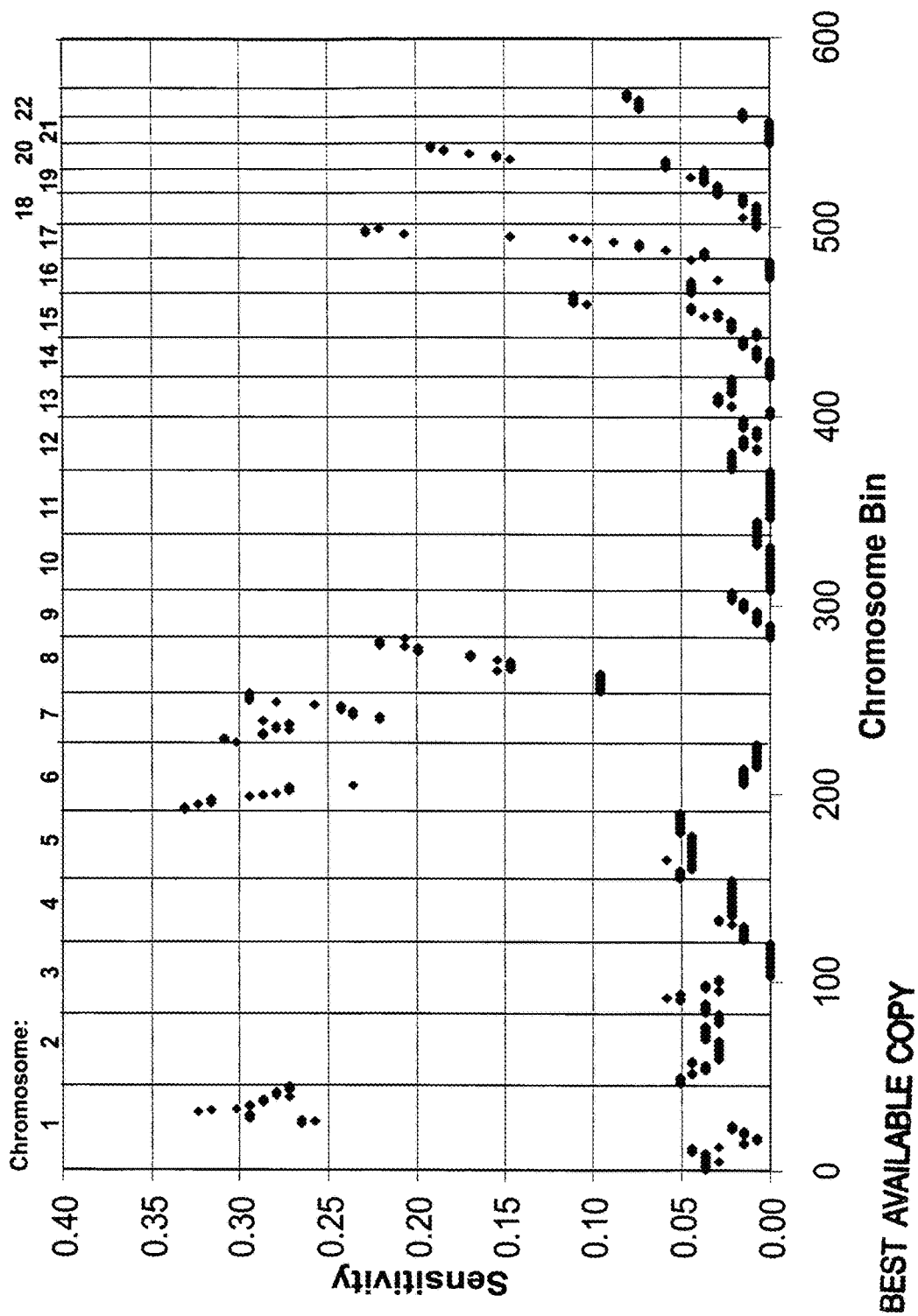

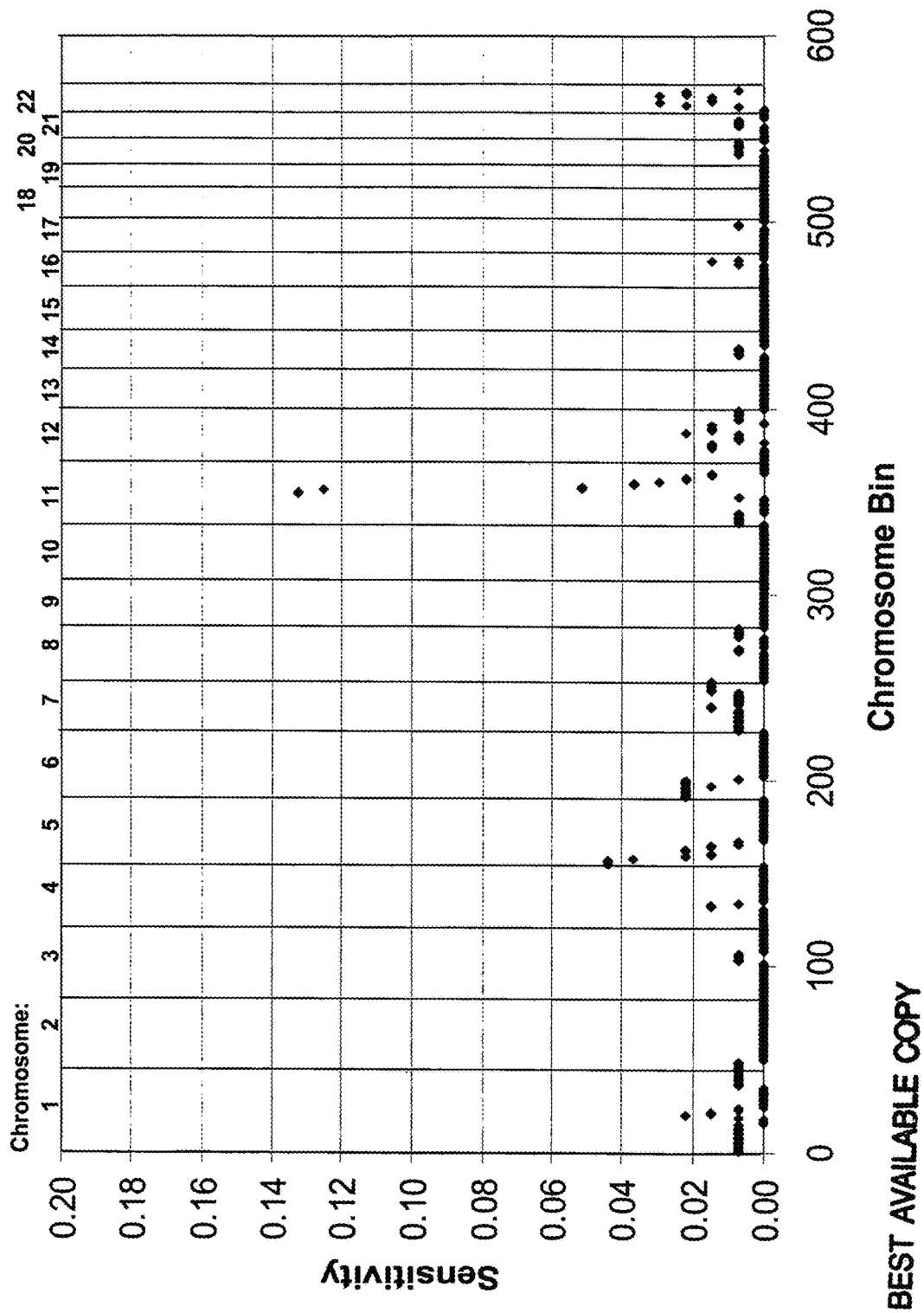

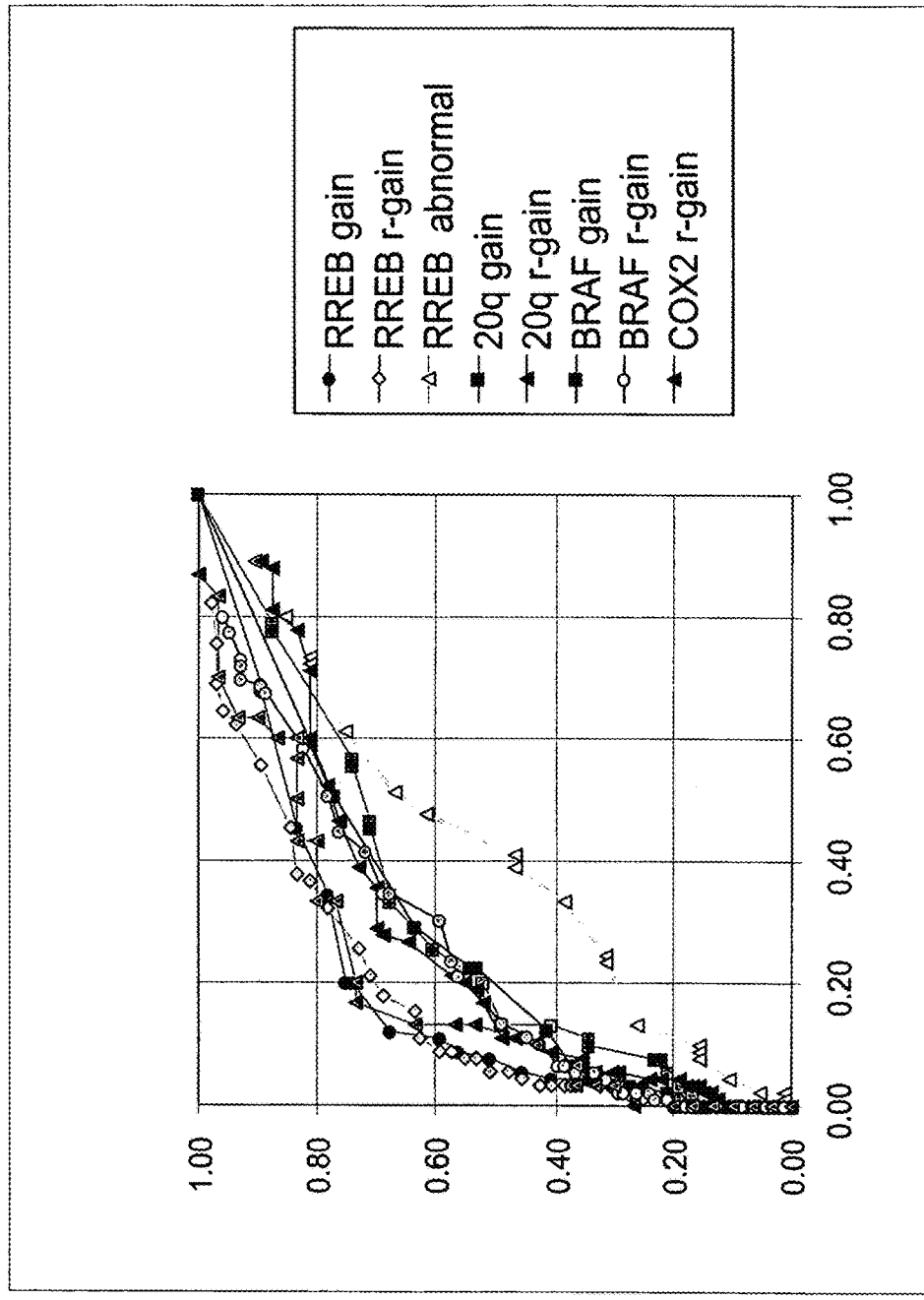
Figure 2A. ROC Curves for Single Probes

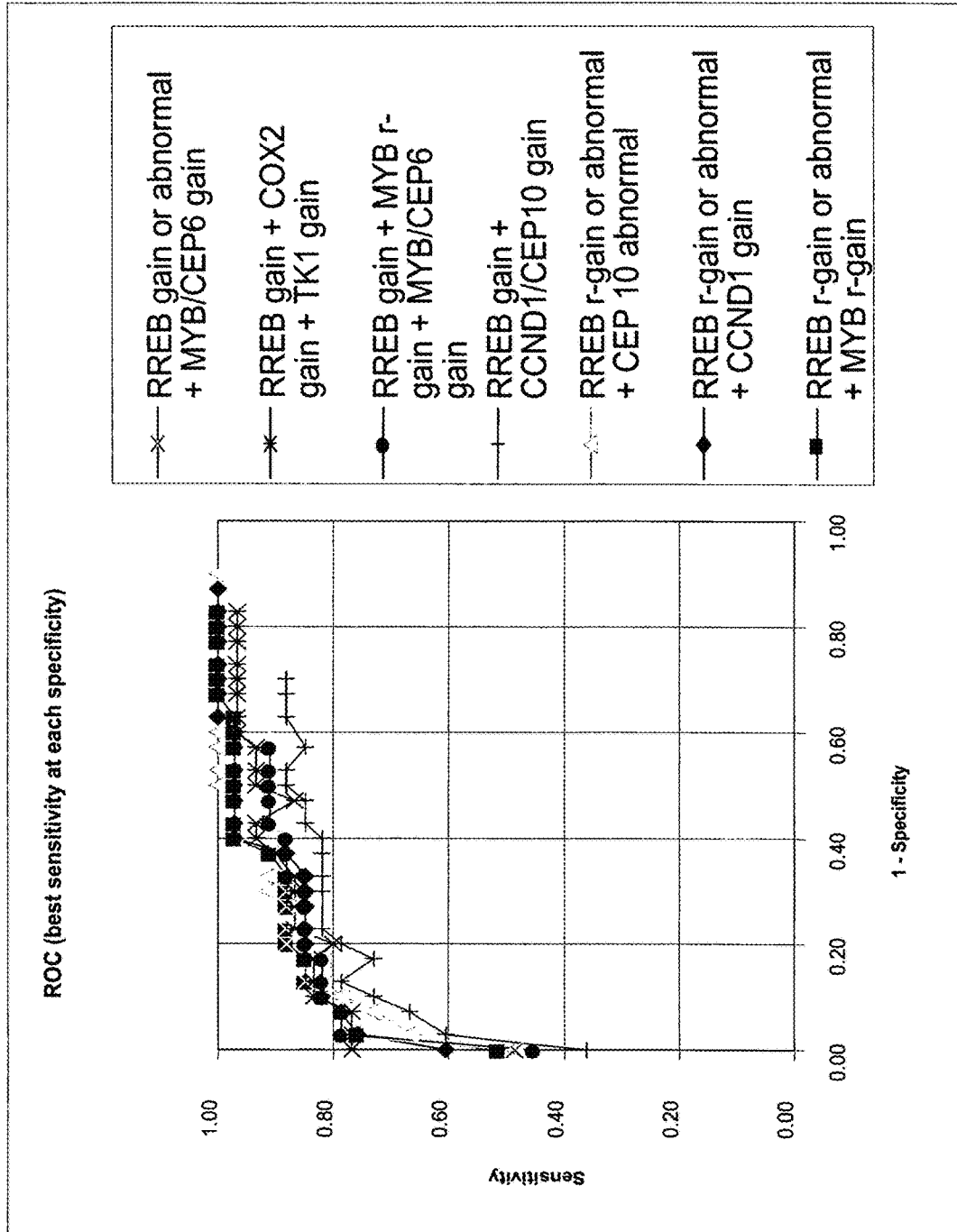
Figure 2B. ROC Curves for Two and Three Probe Combinations

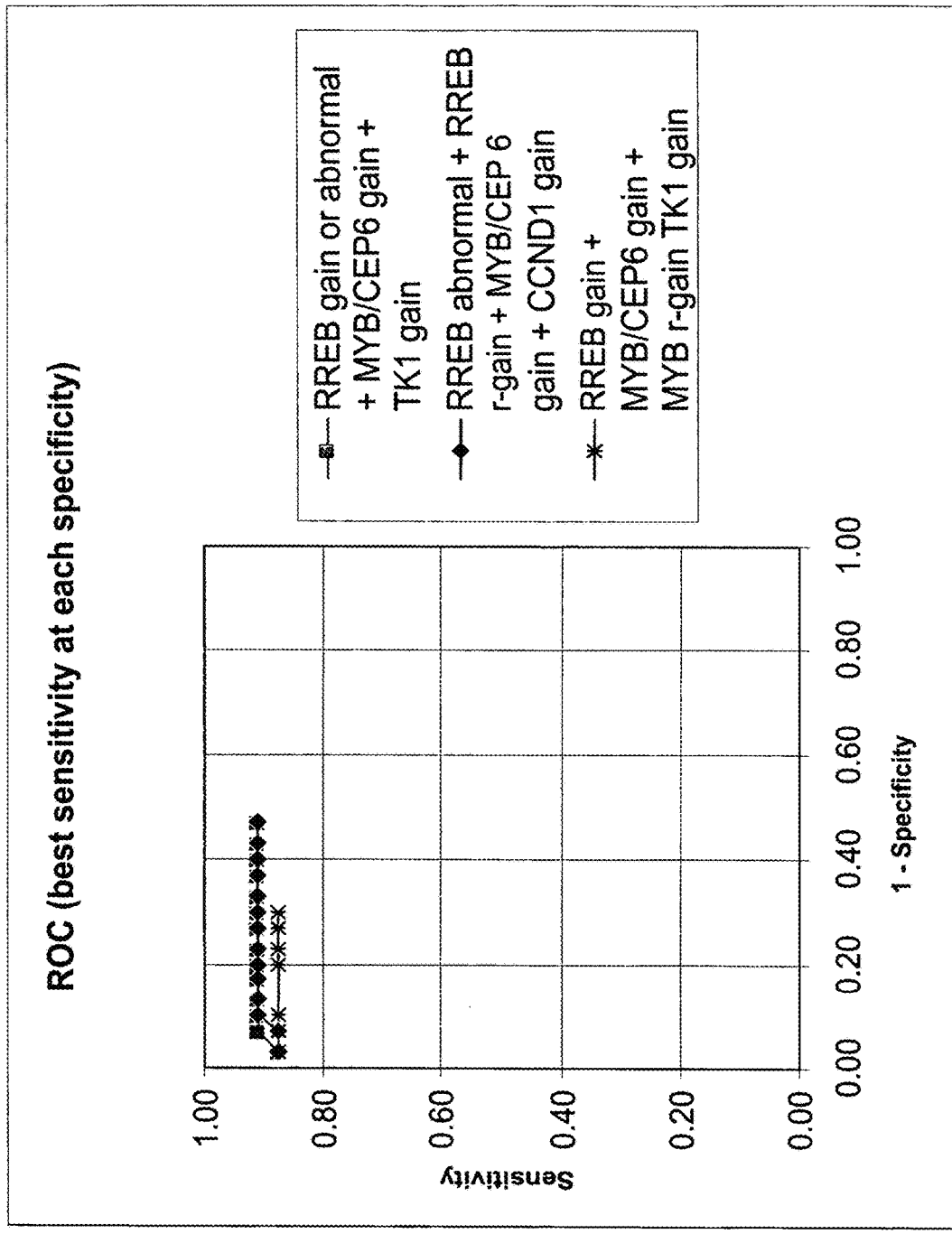
Figure 2C. ROC Curves for Four Probe Combinations.

METHODS AND PROBE COMBINATIONS FOR DETECTING MELANOMA

CROSS-REFERENCE TO RELATED APPLICATIONS

This application is a continuation of U.S. application Ser. No. 11/515,505, filed Sep. 1, 2006, which claims benefit of U.S. provisional application No. 60/713,799, filed Sep. 2, 2005, both of which are incorporated by reference herein in their entireties.

BACKGROUND OF THE INVENTION

Melanoma is an important clinical problem. The incidence and mortality of melanoma has been increasing more rapidly than any other malignancy except lung cancer in women. Pathology is the gold standard for establishing the diagnosis of melanoma. Although many cases can be classified reliably with current pathological criteria, there is a significant subset of cases in which no consensus can be reached even among expert pathologists. The effect of the ambiguity on standard clinical practice is illustrated in a recent study from The Netherlands. An expert panel reviewed 1069 consecutive melanocytic lesions that had been submitted for review by clinical pathologists in order to identify the most common diagnostic problems. In 14% (22/158) of the cases that had been initially classified as invasive melanoma the panel considered the lesions as benign, and in 16.6% (85/513) the panel considered malignant what had been diagnosed as benign (Veenhuizen et al., *J Pathol.* 182:266-72. 1997).

Diagnostic ambiguity has significant adverse consequences for patients. Misclassifying a melanoma as benign may be fatal, and diagnosing a benign lesion as malignant may result in significant morbidity. Current medical practice with equivocal cases usually is to consider them as malignant. However, the morbidity of the therapeutic options—wide re-excision, sentinel lymph node biopsy, and adjuvant alpha-interferon—coupled with the diagnostic uncertainty frequently leads to pursuing a less aggressive treatment regimen. Typically this includes a limited re-excision and close clinical follow-up. Thus patients with benign lesions suffer the side effects of a still significant surgery and the emotional strain of the diagnosis, while those patients that in fact have a melanoma may not receive the optimal treatment. Currently there is no method to definitively resolve these ambiguities. A diagnostic test that could reduce these uncertainties would have a significant positive clinical impact. This invention addresses this need.

Previous studies have shown that melanomas differ from nevi by the presence of frequent gains or losses of particular chromosomal regions. Comparative genomic hybridization (CGH) of primary melanomas has identified losses at 6q, 8p, 9p, and 10q and gains at 1q, 6p, chromosome 7, 8q, 17q, and 20q to be the most common DNA copy number changes in melanoma (Bastian et al, *Am J Pathol.* 163:1765-70, 2003). However, such studies do not provide insight as to a combination of probes that will have a high level of sensitivity and specificity to selectively detect melanoma. The present invention is based on an assessment of the ability of combinations of probes using a multi-color fluorescent in situ hybridization (FISH) test to detect copy number changes of chromosomal regions commonly found to be aberrant in melanoma.

BRIEF SUMMARY OF THE INVENTION

The present invention is based on the discovery of combinations of probes that provide highly sensitive and specific detection of melanoma and thus can distinguish malignant melanoma from benign melanocytic lesions. Methods for the detection of melanoma comprise evaluation of a biological sample from a melanocytic lesion, typically by in situ hybridization, using a set of at least two probes, often a set of at least three probes, and in some embodiments, a set of four probes. Useful probes for detecting melanoma can be selected from the following: a chromosome 6 enumerator probe, a chromosome 7 enumerator probe, a chromosome 8 enumerator probe, a chromosome 9 enumerator probe, a chromosome 10 enumerator probe, a probe that targets chromosome region 17q, a probe that targets chromosome region 10q, a probe that targets chromosome region 6p, a probe that targets chromosome region 6q, a probe that targets chromosome region 9p, a probe that targets chromosome region 8p, a probe that targets chromosome region 8q, a probe that targets chromosome region 1q, a probe that targets chromosome region 7q, a probe that targets chromosome region 20q, and a probe that targets chromosome region 11q. Thus, a probe set of the present invention comprises probes to chromosomal regions selected from the group consisting of 1q, 6p, 6q, 7q, 8p, 8q, 9p, 10q, 11 q, 17q, and 20q. Probe sets can also include chromosomal enumerator probes to chromosomes 6, 7, 8, 9, or 10. Often, useful probe set comprises at least one probe to a chromosomal subregion, e.g., 1q23, 1q31, 6p25, 6q23, 7q34, 8p22, 8q24, 9p21, 10q23, 11q13, 17q25, or 20q13.

In one aspect, the invention provides a method of detecting the presence of melanoma cells in a biological sample from a patient, the method comprising:
a) contacting the sample with a combination of at least two probes, wherein the probes are selected from group consisting of a chromosome 6 enumerator probe, a chromosome 10 enumerator probe, a probe that targets chromosome region 6p (e.g., 6p25), a probe that targets chromosome region 6q (e.g., 6q23), a probe that targets chromosome region 7q (e.g., 7q34), a probe that targets chromosome region 11q (e.g., 11q13), a probe that targets chromosome region 17q (e.g., 17q25), a probe that targets chromosome region 1q (e.g., 1q31), and a probe that targets chromosome region 20q (e.g., 20q13);
b) incubating each probe of the set with the sample under conditions in which each probe binds selectively with a polynucleotide sequence on its target chromosome or chromosomal region to form a stable hybridization complex;
c) detecting and analyzing the hybridization pattern of the combination of probe for the presence or absence of melanoma. A hybridization pattern showing at least one gain or loss or imbalance at a chromosomal region targeted by the probes is indicative of melanoma. The combination of probes typically has a difference from ideal (DFI) value, of about 0.29 or less. In some embodiments, the DFI value is about 0.20 or less. Probe combinations for use in the methods of the invention include 2-, 3-, and 4-probe combinations listed in Table 6 that have a DFI value of about 0.29 or less.

Often, one of the probes in the combination of at least two probes is a probe that targets chromosome subregion 6p25. In some embodiments, a combination of two probes is one probe that targets chromosome subregion 6p25 and a second probe selected from the group consisting of a chromosome 10 enumerator probe, a probe that targets subregion 11q13, and a probe that targets chromosome subregion 6q23.

The methods of the invention can also employ a probe set that has three probes selected from the group consisting of a chromosome 6 enumerator probe, a chromosome 10 enumerator probe, a probe that targets chromosome region 6p (e.g., 6p25), a probe that targets chromosome region 6q (e.g., 6q23), a probe that targets chromosome region 7q (e.g., 7q34), a probe that targets chromosome region 11q (e.g., 11q13), a probe that targets chromosome region 17q (e.g., 17q25), a probe that targets chromosome region 1q (e.g., 1q31), and a probe that targets chromosome region 20q (e.g., 20q13). In some embodiments, one of the three probes in the combination of three probes targets chromosome subregion 6p25. Thus, a combination of three probes for detecting melanoma is often selected from the group of:

a) a probe that targets chromosome subregions 6p25, a probe that targets chromosome subregion 6q23 and a chromosome 6 enumerator probe;
b) a probe that targets chromosome subregion 6p25, a probe that targets chromosome subregion 1q31 and a probe that targets chromosome subregion 17q25;
c) a probe that targets chromosome subregion 6p25, a probe that targets chromosome subregion 11q13 and a chromosome 10 enumerator probe;
d) a probe that targets chromosome subregion 6p25, a probe that targets chromosome subregion 11q13 and a probe that targets chromosome subregion 17q25;
e) a probe that targets chromosome subregion 6p25, a probe that targets chromosome subregion 17q25 and a chromosome 10 enumerator probe;
f) a probe that targets chromosome subregion 6p25, a probe that targets chromosome subregion 1q31 and a chromosome 10 enumerator probe;
g) a probe that targets chromosome subregion 6p25, a probe that targets chromosome subregion 1q31 and a probe that targets chromosome subregion 11q13;
h) a probe that targets chromosome subregion 1q31, a probe that targets chromosome subregion 11q13 and a probe that targets chromosome subregion 17q25;
i) a probe that targets chromosome subregion 6p25, a probe that targets chromosome subregion 7q34 and a probe that targets chromosome subregion 17q25;
j) a probe that targets chromosome subregion 6p25, a probe that targets chromosome subregion 20q13 and a probe that targets chromosome subregion 17q25;
k) a probe that targets chromosome subregion 6p25, a probe that targets chromosome subregion 20q13 and a probe that targets chromosome subregion 11q13;
l) a probe that targets chromosome subregion 6p25, a probe that targets chromosome subregion 20q13 and a probe that targets chromosome subregion 6q23;
m) a probe that targets chromosome subregion 6p25, a probe that targets chromosome subregion 11q13 and a chromosome 10 enumerator probe;
n) a probe that targets chromosome subregion 6p25, a probe that targets chromosome subregion 7q34 and a chromosome 10 enumerator probe; and
o) a probe that targets chromosome subregion 6p25, a probe that targets chromosome subregion 20q13 and a chromosome 10 enumerator probe.

In some embodiments, a combination of at least four probes can be used to detect melanoma, where the probes are selected from the group consisting of a chromosome 6 enumerator probe, a chromosome 10 enumerator probe, a probe that targets chromosome region 6p (e.g., 6p25), a probe that targets chromosome region 6q (e.g., 6q23), a probe that targets chromosome region 7q (e.g., 7q34), a probe that targets chromosome region 11q (e.g., 11q13), a probe that targets chromosome region 17q (e.g., 17q25), a probe that targets chromosome region 1q (e.g., 1q31), and a probe that targets chromosome region 20q (e.g., 20q13). In some embodiments, one of the four probes in the combination targets chromosome subregion 6p25. Thus, a combination of four probes for use in detecting melanoma can be selected from the following group:

a) a probe to chromosome subregions 6p25; a probe to chromosome subregion 6q23, a chromosome 6 enumerator probe, and a chromosome 10 enumerator probe;
b) a probe to chromosome subregions 6p25; a probe to chromosome subregion 6q23, a probe to chromosome subregion 11q13, and a chromosome 6 enumerator probe;
c) a probe to chromosome subregions 6p25; a probe to chromosome subregion 1q31, a probe to chromosome subregion 11q13, and a probe to chromosome subregion 17q25;
d) a probe to chromosome subregions 6p25; a probe to chromosome subregion 6q23, a probe to chromosome subregion 11q13, and a chromosome 10 enumerator probe; and e) a probe to chromosome subregions 6p25; a probe to chromosome subregion 6q23, a probe to chromosome subregion 1q31, and a chromosome 10 enumerator probe;
f) a probe to chromosome subregions 6p25, probe to chromosome subregion 1q31, a probe to chromosome subregion 17q25, and a chromosome 10 enumerator probe;
g) a probe to chromosome subregions 6p25, a probe to chromosome subregion 17q25, a probe to chromosome subregion 6q23, and a chromosome 6 enumerator probe;
h) a probe to chromosome subregions 6p25, a probe to chromosome subregion 20q13, a probe to chromosome subregion 6q23, and a chromosome 6 enumerator probe;
i) a probe to chromosome subregions 6p25, a probe to chromosome subregion 7q34, a probe to chromosome subregion 6q23, and a chromosome 6 enumerator probe;
j) a probe to chromosome subregions 6p25, a probe to chromosome subregion 7q34, a probe to chromosome subregion 1q31, and a probe to chromosome subregion 17q25;
k) a probe to chromosome subregions 6p25, a probe to chromosome subregion 20q13, a probe to chromosome subregion 1q31, and a probe to chromosome subregion 17q25;
l) a probe to chromosome subregions 6p25, a probe to chromosome subregion 7q34, a probe to chromosome subregion 6q23, and a probe to chromosome subregion 17q25;
m) a probe to chromosome subregions 6p25, a probe to chromosome subregion 20q13, a probe to chromosome subregion 6q23, and a probe to chromosome subregion 17q25;
n) a probe to chromosome subregions 6p25, a probe to chromosome subregion 7q34, a probe to chromosome subregion 11q13, and a chromosome 10 enumerator probe;
o) a probe to chromosome subregions 6p25, a probe to chromosome subregion 20q13, a probe to chromosome subregion 11q13, and a chromosome 10 enumerator probe;
p) a probe to chromosome subregions 6p25, a probe to chromosome subregion 7q34, a probe to chromosome subregion 17q25, and a probe to chromosome subregion 11q13;

q) a probe to chromosome subregions 6p25, a probe to chromosome subregion 20q13, a probe to chromosome subregion 17q25, and a probe to chromosome subregion 11q13;

r) a probe to chromosome subregions 6p25, a probe to chromosome subregion 7q34, a probe to chromosome subregion 17q25, and a chromosome 10 enumerator probe;

s) a probe to chromosome subregions 6p25, a probe to chromosome subregion 20q13, a probe to chromosome subregion 17q25, and a chromosome 10 enumerator probe;

t) a probe to chromosome subregions 6p25, a probe to chromosome subregion 7q34, a probe to chromosome subregion 20q13, and a probe to chromosome subregion 17q25;

u) a probe to chromosome subregions 6p25, a probe to chromosome subregion 6q23, a probe to chromosome subregion 17q25, and a chromosome 10 enumerator probe;

v) a probe to chromosome subregions 6p25, a probe to chromosome subregion 17q25, a probe to chromosome subregion 11q13, and a chromosome 10 enumerator probe; and x) a probe to chromosome subregion 17q25, a probe to chromosome subregion 7q34, a probe to chromosome subregion 6q23, and a chromosome 6 enumerator probe.

Probe combinations are not limited to those that comprise probes that target the exemplary subregions, supra. Any probe that targets the chromosome region of interest can be used.

In typical embodiments, the melanoma detection methods of the invention employ a skin sample, such as a skin biopsy sample. In some embodiments, the biological sample may be a formalin-fixed, paraffin-embedded sample. The biological sample is hybridized under conditions in which the members of the probe set selectively hybridize to the target chromosome or chromosome region/subregion. The probes are often labeled with fluorescent labels. In some embodiments, hybridization of the probe set is performed concurrently, i.e., the probes are hybridized at the same time to the same sample. The hybridization pattern of the probe set is evaluated to determine whether malignant melanoma cells are present in the lesion.

The invention also provides combinations of probes (two-, three-, or four-probe combinations) for diagnosing melanoma and kits that contain such combinations of probes. The probes that are members of the combinations are selected from the group consisting of a chromosome 6 enumerator probe, a chromosome 10 enumerator probe, a probe that targets chromosome region 6p (e.g., 6p25), a probe that targets chromosome region 6q (e.g., 6q23), a probe that targets chromosome region 11q (e.g., 11q13), a probe that targets chromosome region 17q (e.g., 17q25), and a probe that targets chromosome region 1q (e.g., 1q31). Typically, a combination of probes of the invention has a DFI value of less than about 0.29 for melanoma. Often, the combination of probes has a DFI of less than about 0.2. A set of probes of the invention is thus any of the two-, three-, or four-probe combinations specifically set forth above.

BRIEF DESCRIPTION OF THE DRAWINGS

FIGS. 1A, 1B, and 1C show analysis of the CGH melanoma data for the sensitivity of individual loci to detect melanoma. The plots show the entire genome from the p arm of chromosome 1 to the q arm of chromosome 22 binned by chromosome band position along the x-axis. The y-axis shows the specificity. FIG. 1A shows the sensitivity for DNA copy number losses. FIG. 1B shows the sensitivity for DNA copy number losses gains. FIG. 1C shows the sensitivity for DNA copy number amplifications.

FIGS. 2A, 2B, and 2C provide exemplary ROC curves for several combinations of probes.

DETAILED DESCRIPTION OF THE INVENTION

The terms "melanoma" or "cutaneous melanoma" or "malignant melanoma" refer to malignant neoplasms of melanocytes, which are pigment cells present normally in the epidermis, in adnexal structures including hair follicles, and sometimes in the dermis, as well as extracutaneous sites such as the mucosa, meninx, conjuctiva, and uvea. There are at least four types of cutaneous melanoma: lentigo maligna melanoma, superficial spreading melanoma (SSM), nodular melanoma, and acral lentiginous melanoma (AM). Cutaneous melanoma typically starts as a proliferation of single melanocytes, e.g., at the junction of the epidermis and the dermis. The cells first grow in a horizontal manner and settle an area of the skin that can vary from a few millimeters to several centimeters. As noted above, in most instances the transformed melanocytes produce increased amounts of pigment so that the area involved can easily be seen by the clinician.

The term "melanocytic lesion" refers to an accumulation of melanocytes that can undergo a benign, locally aggressive, or malignant course. "Melanocytic lesion" encompasses both benign melanocytic neoplasms, such as "nevi" and "lentigines" and "melanocytomas"; malignant melanocytic neoplasms, and "melanoma" and "malignant blue nevus".

The terms "tumor" or "cancer" in an animal refers to the presence of cells possessing characteristics such as atypical growth or morphology, including uncontrolled proliferation, immortality, metastatic potential, rapid growth and proliferation rate, and certain characteristic morphological features. Often, cancer cells will be in the form of a tumor, but such cells may exist alone within an animal. "Tumor" includes both benign and malignant neoplasms. The term "neoplastic" refers to both benign and malignant atypical growth.

The terms "hybridizing specifically to", "specific hybridization", and "selectively hybridize to," as used herein refer to the binding, duplexing, or hybridizing of a nucleic acid molecule preferentially to a particular nucleotide sequence under stringent conditions. The term "stringent conditions" refers to conditions under which a probe will hybridize preferentially to its target subsequence, and to a lesser extent to, or not at all to, other sequences. A "stringent hybridization" and "stringent hybridization wash conditions" in the context of nucleic acid hybridization (e.g., as in array, Southern or Northern hybridizations) are sequence dependent, and are different under different environmental parameters. An extensive guide to the hybridization of nucleic acids is found in, e.g., Tijssen (1993) *Laboratory Techniques in Biochemistry and Molecular Biology—Hybridization with Nucleic Acid Probes* part I, Ch. 2, "*Overview of principles of hybridization and the strategy of nucleic acid probe assays*," Elsevier, N.Y. ("Tijssen"). Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on an array or on a filter in a Southern or northern blot is 42° C. using standard hybridization solutions (see, e.g., Sambrook and Russell (2001) *Molecular Cloning: A Laboratory Manual* (3rd ed.) Vol. 1-3, Cold Spring Harbor Laboratory, Cold Spring Harbor Press, NY, and detailed discussion, below).

The term "nucleic acid" as used herein refers to a deoxyribonucleotide or ribonucleotide in either single- or double-stranded form. The term encompasses nucleic acids, i.e., oligonucleotides, containing known analogues of natural nucleotides which have similar or improved binding properties, for the purposes desired, as the reference nucleic acid. The term also includes nucleic acids which are metabolized in a manner similar to naturally occurring nucleotides or at rates that are improved for the purposes desired. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) *J. Med. Chem.* 36:1923-1937; Antisense Research and Applications (1993, CRC Press). PNAs contain non-ionic backbones, such as N-(2-aminoethyl) glycine units. Phosphorothioate linkages are described in WO 97/03211; WO 96/39154; Mata (1997) *Toxicol. Appl. Pharmacol.* 144:189-197. Other synthetic backbones encompassed by the term include methyl-phosphonate linkages or alternating methylphosphonate and phosphodiester linkages (Strauss-Soukup (1997) *Biochemistry* 36: 8692-8698), and benzylphosphonate linkages (Samstag (1996) *Antisense Nucleic Acid Drug Dev* 6: 153-156). The term nucleic acid is used interchangeably with gene, cDNA, mRNA, oligonucleotide primer, probe and amplification product.

The term "biological sample" or "specimen" is intended to mean a sample obtained from a patient suspected of having, or having melanoma. Typically, the sample comprises a formalin-fixed paraffin-embedded skin biopsy of a body region suspected to contain melanoma cells. In addition to patients suspected of having melanoma, the biological sample may further be derived from a subject that has been diagnosed with melanoma for confirmation of diagnosis or establishing that all of the tumor was removed ("clear margin"). In addition, the biological sample may be derived from non-skin tissue such as lymph nodes to establish whether any melanocytes present in this tissue represent melanoma or nevus. The biological sample may be derived from a subject with an ambiguous diagnosis in order to clarify the diagnosis. The sample may be derived from a "punch", "shave", curettage, fine needle aspirate, sentinel lymph node or excisional biopsy, or other excision of the region including the suspected lesion or peripheral to the suspected or known lesion in order to establish a clear margin.

Introduction

The current invention is based, in part, on the identification of highly sensitive and specific chromosomal probe sets that can be used to selectively detect melanoma. The probe sets provide higher sensitivity and specificity than individual probes. The invention thus provides methods and compositions for the use of such probe sets. The probes encompass locus-specific probes as well as chromosome enumeration probes, which typically hybridize to centromeric regions.

Chromosomal Probes

Probes for use in the invention are used for hybridization to nucleic acids that are present in biological samples from patients that have a melanocytic tumor for which some degree of suspicion exists that it could be melanoma. In situ hybridization is usually employed in the methods of the invention. In typical embodiments, the probes are labeled with fluorescent labels.

A "chromosomal probe" or "chromosomal probe composition" refers to one or more polynucleotides that specifically hybridize to a region of a chromosome. The target sequences to which the probe can bind vary in length, typically from about 70,000 nucleotides to about 800,000 nucleotides. Smaller probes, e.g., that hybridize to a region of less than 100,000 nucleotides; or to a region of less than 10,000 nucleotides, can also be employed.

A probe to a particular chromosomal region can comprise multiple polynucleotide fragments, e.g., ranging in size from about 50 to about 1,000 nucleotides in length.

Chromosome Enumeration Probe

A chromosome enumeration probe is any probe able to enumerate the number of specific chromosomes in a cell. A chromosome enumeration probe typically recognizes and binds to a region near to (referred to as "peri-centromeric") or at the centromere of a specific chromosome, typically a repetitive DNA sequence. The centromere of a chromosome is typically considered to represent that chromosome entity since the centromere is required for faithful segregation during cell division. Deletion or amplification of a particular chromosomal region can be differentiated from loss or gain of the whole chromosome (aneusomy), within which it normally resides, by comparing the number of FISH signals corresponding to the particular locus (copy number) to the number of signals for the corresponding centromere. One method for making this comparison is to divide the number of signals representing the locus by the number of signals representing the centromere. Ratios of less than one indicate relative loss or deletion of the locus, and ratios greater than one indicate relative gain or amplification of the locus. Similarly, comparison can be made between two different loci on the same chromosome, for example on two different arms of the chromosome, to indicate imbalanced gains or losses within the chromosome.

In lieu of a centromeric probe for a chromosome, one of skill in the art will recognize that a chromosomal arm probe may alternately be used to approximate whole chromosomal loss or gain. However, such probes are not as accurate at enumerating chromosomes since the loss of signals for such probes may not always indicate a loss of the entire chromosomes. Examples of chromosome enumeration probes include CEP® probes (e.g., CEP® 12 and X/Y probes) commercially available from Abbott Molecular, DesPlaines, Ill. (formerly Vysis, Inc., Downers Grove, Ill.).

Chromosome enumerator probes and locus-specific probes that target a chromosome region or subregion can readily be prepared by those in the art or can be obtained commercially, e.g., from Abbott Molecular, Molecular Probes, Inc. (Eugene, Oreg.), or Cytocell (Oxfordshire, UK).

Such probes are prepared using standard techniques Chromosomal probes may be prepared, for example, from protein nucleic acids, cloned human DNA such as plasmids, bacterial artificial chromosomes (BACs), and P1 artificial chromosomes (PACs) that contain inserts of human DNA sequences. A region of interest may be obtained via PCR amplification or cloning. Alternatively, chromosomal probes may be prepared synthetically.

Locus-Specific Probes

Probes that can be used in the invention include probes that selectively hybridize to chromosome regions (e.g., 1q, 6p, 6q, 7q, 11q, 17q, and 20q) or subregions of the chromosome regions (e.g., 1q23, 1q31, 6p25, 6q23, 7q34, 11q13, 17q25, or 20q13). Such probes are also referred to as locus-specific probes. Locus-specific probe targets preferably comprise at least 100,000 nucleotides. A locus-specific probe selectively binds to a specific locus at a chromosomal region that is known to undergo gain or loss in melanoma. A probe can target coding or non-coding regions, or both, including exons, introns, and/or regulatory sequences, such as promoter sequences and the like.

When targeting of a particular gene locus is desired, probes that hybridize along the entire length of the targeted gene are preferred although not required. For cells of a given sample, relative to those of a control, increases or decreases in the number of signals for a probe indicate a gain or loss, respectively, for the corresponding region. In some embodiments, a locus-specific probe can be designed to hybridize to an oncogene or tumor suppressor gene, the genetic aberration of which is correlated with melanoma. Locus-specific probes can hybridize to loci on chromosomal regions including, for example, 8q24, 9p21, 17q, and 20q13. Exemplary, locus-specific probes that target these regions are probes to C-MYC, P16, HER2, and ZNF217, respectively.

Probes for use in the invention target region on chromosomal arms (also referred to herein as a chromosomal region) that undergo gain or loss in melanoma, e.g., 17q, 10q, 6p, 6q, 1q, 7q, 11q and 20q. Gain or loss can be determined using any probe that targets the chromosome arm of interest. Often, probes that target subregions, e.g., 17q25, 10q23, 6p25, 6q23, 1q23, 1q31, 7q34, 11q13 or 20q13, are employed. In the context of this invention, probes to the chromosomal subregions noted herein are representative of the chromosomal arm of interest. Further, the subregion designations as used herein include the designated band and typically about 10 megabases of genomic sequence to either side.

Probe Selection Methods

Probe sets can be selected for their ability to simply detect melanoma, but are typically selected for the ability to discriminate between melanoma and other benign melanocytic lesions. Thus, analyses of probe sets are typically performed to determine the DFI values of different probe sets for discriminating between melanoma and benign nevi.

Probe sets for use in the methods of the present invention can be selected using the principles described in the examples. Combinations of chromosomal probes within a probe set are chosen for sensitivity, specificity, and detectability regarding melanoma. Sensitivity refers to the ability of a test (e.g. FISH) to detect disease (e.g. melanoma) when it is present. More precisely, sensitivity is defined as True Positives/(True Positives+False Negatives). A test with high sensitivity has few false negative results, while a test with low sensitivity has many false negative results. Specificity, on the other hand, refers to the ability of test (e.g. FISH) to give a negative result when disease is not present. More precisely, specificity is defined as True Negatives/(True Negatives+False Positives). A test with high specificity has few false positive results, while a test with a low specificity has many false positive results.

In general, chromosomal probe sets with the highest combined sensitivity and specificity for the detection of melanoma are to be chosen. The combined sensitivity and specificity of a probe set can be represented by the parameter distance from ideal (DFI), defined as $[(1-\text{sensitivity})^2+(1-\text{specificity})^2]^{1/2}$. DFI values range from 0 to 1.414, with 0 representing a probe set having 100% sensitivity and 100% specificity and 1.414 representing a probe set with 0% sensitivity and 0% specificity. In this invention, probe sets chosen for the identification of melanoma will have DFI values that are at most about 0.29. Probe sets that have DFI values of less than about 0.20 usually provide better results.

There is no limit to the number of probes that can be employed in a set, however, in some embodiments, the number of probes within a set that is to be viewed by a human observer (and not with computer assisted imaging techniques) may be restricted for practical reasons, e.g., by the number of unique fluorophores that provide visually distinguishable signals upon hybridization. For example, typically four or five unique fluorophores (e.g., which appear as red, green, aqua, and gold signals to the human eye) can be conveniently employed in a single probe set. Generally, the sensitivity of an assay increases as the number of probes within a set increases. However, the increases in sensitivity become smaller and smaller with the addition of more probes and at some point the inclusion of additional probes to a probe set is not associated with significant increases in the sensitivity of the assay ("diminishing returns"). Increasing the number of probes in a probe set may decrease the specificity of the assay. Accordingly, a probe set of the present invention typically comprises two, three, or four chromosomal probes, as necessary to provide optimal balance between sensitivity and specificity.

Individual probes are chosen for inclusion in a probe set of the present invention based on their ability to complement other probes within the set. Specifically, they are targeted to chromosomes or chromosomal subregions that are not frequently altered simultaneously within a given melanoma. Thus, each probe in a probe set complements the other(s), i.e., identifies melanoma where the other probes in the set sometime fail to identify. One method for determining which probes complement one another is to identify single probes with the lowest DFI values for a group of tumor specimens. Then additional probes can be tested on the tumor samples that the initial probe failed to identify, and the probe with the lowest DFI value measured in combination with the initial probe(s) is added to the set. This may then be repeated until a full set of chromosomal probes with the desired DFI value is achieved.

Discrimination analysis is one method that can be used to determine which probes are best able to detect melanoma. This method assesses if individual probes are able to detect a statistically different percentage of abnormal cells in test specimens (e.g. melanoma) when compared to normal specimens. The detection of cells with chromosomal (or locus) gains or chromosomal (or locus) losses can both be used to identify neoplastic cells in melanoma patients with melanocytic lesions. However, chromosomal losses sometimes occur as an artifact in normal cells because of random signal overlap and/or poor hybridization. In sections of formalin-fixed paraffin-embedded material, commonly used to assess skin biopsies, truncation of nuclei in the sectioning process can also produce artifactual loss of chromosomal material.

Consequently, chromosomal gains are often a more reliable indicator of the presence of neoplastic cells.

Cutoff values for individual chromosomal gains and losses must be determined when choosing a probe set. The term "cutoff value" is intended to mean the value of a parameter associated with chromosomal aberration that divides a population of specimens into two groups—those specimens above the cutoff value and those specimens below the cutoff value. For example, the parameter may be the absolute number or percentage of cells in a population that have genetic aberrations (e.g., losses or gains for target regions). If the number or percentage of cells in the specimen harboring losses or gains for a particular probe is higher than the cutoff value, the sample is determined to be positive for melanoma.

A useful probe set often comprises a probe to a chromosomal region selected from the group consisting of 1q23, 1q31, 6p25, 6q23, 7q34, 11q13, 17q25, and 20q13, and/or chromosome enumeration probes for chromosomes 6 and 10, e.g., CEP® 6, and CEP® 10, available from Abbott Molecular Inc. Such probe sets detect the presence of melanoma and can discriminate melanoma from benign specimens.

A probe set able to detect melanoma and/or discriminate melanoma from benign specimens may comprise two or more probes selected from the group of probes targeting 1q23, 1q31, 6p25, 6q23, 7q34, 11q13, 17q25, 20q13, or a chromosome enumerator probe, e.g., to the peri-centromeric regions of chromosomes 6 or 10. In some embodiments, the probe set comprises probes to: a) 6p25 and a chromosome 10 enumerator, b) 6p25 and 11q13, c) 6p25 and 6q23, d) 6p25 and 20q13, e) a chromosome 10 enumerator and 1q31, f) 6p25 and 1q31, g) 6q23 and 1q31, h) 7q34 and 6p25, i) 6q23 and 1q23, j) 6q23, 6p25 and a chromosome 6 enumerator, k) 6p25, 1q31 and 17q25, l) 11q13, 6p25 and a chromosome 10 enumerator, m) 6p25, 11q13, and 17q25, n) 6p25, 1q31, and a chromosome 10 enumerator, o) 6p25, 1q31, and 11q13, p) 1q31, 11q13, and 17q25, q) 6q23, 6p25, and 11q13, r) 20q13, 7 q34, and 6p25 s) 6p25, 6q23, a chromosome 6 enumerator, and a chromosome 10 enumerator, u) 6p25, 1q31, 11q13, and 17q25, v) 6p25, 1q31, a chromosome 10 enumerator, and 17q25, w) 11q13, a chromosome 10 enumerator, 6q23, and 6p25, x) 6q23, 6p25, 1q31, and a chromosome 10 enumerator, or y) 6q23, a chromosome 6 enumerator, 6p25 and 11q13.

Probe Hybridization

Conditions for specifically hybridizing the probes to their nucleic acid targets generally include the combinations of conditions that are employable in a given hybridization procedure to produce specific hybrids, the conditions of which may easily be determined by one of skill in the art. Such conditions typically involve controlled temperature, liquid phase, and contact between a chromosomal probe and a target. Hybridization conditions vary depending upon many factors including probe concentration, target length, target and probe G-C content, solvent composition, temperature, and duration of incubation. At least one denaturation step must precede contact of the probes with the targets. Alternatively, both the probe and nucleic acid target may be subjected to denaturing conditions together while in contact with one another, or with subsequent contact of the probe with the biological sample. Hybridization may be achieved with subsequent incubation of the probe/sample in, for example, a liquid phase of about a 50:50 volume ratio mixture of 2-4×SSC and formamide, at a temperature in the range of about 25 to about 55° C. for a time that is illustratively in the range of about 0.5 to about 96 hours, or more preferably at a temperature of about 32 to about 40° C. for a time in the range of about 2 to about 16 hours. In order to increase specificity, use of a blocking agent such as unlabeled blocking nucleic acid as described in U.S. Pat. No. 5,756,696, the contents of which are herein incorporated by reference, may be used in conjunction with the methods of the present invention. Other conditions may be readily employed for specifically hybridizing the probes to their nucleic acid targets present in the sample, as would be readily apparent to one of skill in the art.

Upon completion of a suitable incubation period, non-specific binding of chromosomal probes to sample DNA may be removed by a series of washes. Temperature and salt concentrations are suitably chosen for a desired stringency. The level of stringency required depends on the complexity of a specific probe sequence in relation to the genomic sequence, and may be determined by systematically hybridizing probes to samples of known genetic composition. In general, high stringency washes may be carried out at a temperature in the range of about 65 to about 80° C. with about 0.2× to about 2×SSC and about 0.1% to about 1% of a non-ionic detergent such as Nonidet P-40 (NP40). If lower stringency washes are required, the washes may be carried out at a lower temperature with an increased concentration of salt.

Detection of Probe Hybridization Patterns

The hybridization probes can be detected using any means known in the art. Label-containing moieties can be associated directly or indirectly with chromosomal probes. The term "label containing moiety" or "detection moiety" generally refers to a molecular group or groups associated with a chromosomal probe, either directly or indirectly, that allows for detection of that probe upon hybridization to its target. Different label containing moieties are selected for each individual probe within a particular set so that each hybridized probe is visually distinct from the others upon detection. Preferably, fluorescence in situ hybridization (FISH) is employed and the chromosomal probes are labeled with distinct fluorescent label-containing moieties. Fluorophores, organic molecules that fluoresce upon irradiation at a particular wavelength, are typically directly attached to the chromosomal probes. A large number of fluorophores are commercially available in reactive forms suitable for DNA.

Attachment of fluorophores to nucleic acid probes is well known in the art and may be accomplished by any available means. Fluorophores can be covalently attached to a particular nucleotide, for example, and the labeled nucleotide incorporated into the probe using standard techniques such as nick translation, random priming, PCR labeling, and the like. Alternatively, the fluorophore can be covalently attached via a linker to the deoxycytidine nucleotides of the probe that have been transaminated. Methods for labeling probes are described in U.S. Pat. No. 5,491,224 and Molecular Cytogenetics: Protocols and Applications (2002), Y.-S. Fan, Ed., Chapter 2, "Labeling Fluorescence In Situ Hybridization Probes for Genomic Targets," L. Morrison et al., p. 21-40, Humana Press, both references of which are herein incorporated by reference.

Exemplary fluorophores that can be used for labeling probes include TEXAS RED (Molecular Probes, Inc., Eugene, Oreg.), CASCADE blue aectylazide (Molecular Probes, Inc., Eugene, Oreg.), SpectrumOrange™ (Abbott Molecular, Des Plaines, Ill.) and SpectrumGold™ (Abbott Molecular).

One of skill in the art will recognize that other agents or dyes can be used in lieu of fluorophores as label-containing moieties. Luminescent agents include, for example, radioluminescent, chemiluminescent, bioluminescent, and phosphorescent label containing moieties. Alternatively, detection moieties that are visualized by indirect means can be used. For example, probes can be labeled with biotin or digoxygenin using routine methods known in the art, and then further processed for detection. Visualization of a biotin-containing probe can be achieved via subsequent binding of avidin conjugated to a detectable marker. The detectable marker may be a fluorophore, in which case visualization and discrimination of probes may be achieved as described above for FISH.

Chromosomal probes hybridized to target regions may alternatively be visualized by enzymatic reactions of label moieties with suitable substrates for the production of insoluble color products. Each probe may be discriminated from other probes within the set by choice of a distinct label moiety. A biotin-containing probe within a set may be detected via subsequent incubation with avidin conjugated to alkaline phosphatase (AP) or horseradish peroxidase (HRP) and a suitable substrate. 5-bromo-4-chloro-3-indolylphosphate and nitro blue tetrazolium (NBT) serve as substrates for alkaline phosphatase, while diaminobenzidine serves as a substrate for HRP.

In embodiments where fluorophore-labeled probes or probe compositions are used, the detection method can involve fluorescence microscopy, flow cytometry, or other means for determining probe hybridization. Any suitable microscopic imaging method may be used in conjunction with the methods of the present invention for observing multiple fluorophores. In the case where fluorescence microscopy is employed, hybridized samples may be viewed under light suitable for excitation of each fluorophore and with the use of an appropriate filter or filters. Automated digital imaging systems such as the MetaSystems, BioView or Applied Imaging systems may alternatively be used.

Screening and Diagnosis of Patients for Melanoma

The detection methods of the invention comprise obtaining a biological sample from a subject having melanoma or suspected of having melanoma. The biological sample is typically a tissue sample that comprises the melanocytic lesion. Often, the biological sample is formalin-fixed and paraffin embedded. The sample is contacted with chromosomal probes to selectively detect melanoma in the sample, if any, under conditions for specifically hybridizing the probes to their nucleic acid targets present in the sample. The probes of the set can be hybridized concurrently or sequentially with the results of each hybridization imaged digitally, the probe or probes stripped, and the sample thereafter hybridized with the remaining probe or probes. Multiple probe sets can also be hybridized to the sample in this manner.

The biological sample can be from a patient suspected of having melanoma or from a patient diagnosed with melanoma, e.g., for confirmation of diagnosis or establishing a clear margin, or for the detection of melanoma cells in other tissues such as lymph nodes. The biological sample can also be from a subject with an ambiguous diagnosis in order to clarify the diagnosis. The biological sample can also be from a subject with a histopathologically benign lesion to confirm the diagnosis. Biological samples can be obtained using any of a number of methods in the art. Examples of biological samples comprising potential melanocytic lesions include those obtained from excised skin biopsies, such as punch biopsies, shave biopsies, fine needle aspirates, or surgical excisions; or biopsy from non-cutaneous tissues such as lymph node tissue, mucosa, meninx, conjuctiva, or uvea. In other embodiments, the biological sample can be obtained by shaving, waxing, or stripping the region of interest on the skin.

As noted, a biological sample can be treated with a fixative such as formaldehyde and embedded in paraffin and sectioned for use in the methods of the invention. Alternatively, fresh or frozen tissue can be pressed against glass slides to form monolayers of cells known as touch preparations, which contain intact nuclei and do not suffer from the truncation artifact of sectioning. These cells may be fixed, e.g., in alcoholic solutions such as 100% ethanol or 3:1 methanol:acetic acid. Nuclei can also be extracted from thick sections of paraffin-embedded specimens to reduce truncation artifacts and eliminate extraneous embedded material. Typically, biological samples, once obtained, are harvested and processed prior to hybridization using standard methods known in the art. Such processing typically includes protease treatment and additional fixation in an aldehyde solution such as formaldehyde.

Prescreening of Samples

Prior to detection, cell samples may be optionally pre-selected based on apparent cytologic abnormalities as disclosed in U.S. Pat. No. 6,174,681, the contents of which are herein incorporated by reference. Pre-selection identifies suspicious cells, thereby allowing the screening to be focused on those cells. Pre-selection allows for faster screening and increases the likelihood that a positive result will not be missed. During pre-selection, cells from a biological sample are placed on a microscope slide and visually scanned for cytologic abnormalities commonly associated with dysplastic and neoplastic cells. Such abnormalities include abnormalities in nuclear size, nuclear shape, and nuclear staining, as assessed by counterstaining nuclei with nucleic acid stains or dyes such as propidium iodide or 4,6-diamidino-2-phenylindole dihydrochloride (DAPI) usually following hybridization of probes to their target DNAs. Typically, neoplastic cells harbor nuclei that are enlarged, irregular in shape, and/or show a mottled staining pattern. Propidium iodide, typically used at a concentration of about 0.4 µg/ml to about 5 µg/ml, is a red-fluorescing DNA-specific dye that can be observed at an emission peak wavelength of 614 nm. DAPI, typically used at a concentration of about 125 ng/ml to about 1000 ng/ml, is a blue fluorescing DNA-specific stain that can be observed at an emission peak wavelength of 452 nm. In this case, only those cells pre-selected for detection are subjected to counting for chromosomal losses and/or gains. Preferably, pre-selected cells on the order of at least 20, and more preferably at least 30-40, in number are chosen for assessing chromosomal losses and/or gains. Preselection of a suspicious region on a tissue section may be performed on a serial section stained by conventional means, such as H&E or PAP staining, and the suspect region marked by a pathologist or otherwise trained technician. The same region is then located on the serial section stained by FISH and nuclei enumerated within that region. Within the marked region, enumeration may be limited to nuclei exhibiting abnormal characteristics as described above.

Alternatively, cells for detection may be chosen independent of cytologic or histologic features. For example, all non-overlapping cells in a given area or areas on a microscope slide may be assessed for chromosomal losses and/or gains. As a further example, cells on the slide, e.g., cells that show altered morphology, on the order of at least about 50, and more preferably at least about 100, in number that appear in consecutive order on a microscope slide may be chosen for assessing chromosomal losses and/or gains.

Hybridization Pattern

The term "target region" or "nucleic acid target" refers to a nucleotide sequence that resides at a specific chromosomal location whose loss and/or gain is indicative of the presence of melanoma. The "target region" or "nucleic acid target" is to be specifically recognized by a probe of the present invention and hybridize to the same in the method of the present invention.

The hybridization pattern for the set of chromosomal probes to the target regions is detected and recorded for cells chosen for assessment of chromosomal losses and/or gains. Hybridization is detected by the presence or absence of the particular signals generated by each of the chromosomal probes. The term "hybridization pattern" is intended to refer to the quantification of chromosomal losses/gains for those cells chosen for such assessment, relative to the number of the same in an evenly matched control sample, for each probe throughout a chosen cell sample. The quantification of losses/gains can include determinations that evaluate the ratio of one locus to another on the same or a different chromosome. Once the number of target regions within each cell is determined, as assessed by the number of regions showing hybridization to each probe, relative chromosomal gains and/or losses may be quantified. A relative gain or loss for each probe is determined by comparing the number of distinct probe signals in each cell to the number expected in a normal cell, i.e., where the copy number should be two. Non-neoplastic cells in the sample, such as keratinocytes, fibroblasts, and lymphocytes, can be used as reference normal cells. More than the normal number of probe signals is considered a gain, and fewer than the normal number is considered a loss. Alternatively, a minimum number of signals per probe per cell can be required to consider the cell abnormal (e.g., 5 or more signals). Likewise for loss, a maximum number of signals per probe can be required to consider the cell abnormal (e.g., 0 signals, or one or fewer signals).

The percentages of cells with at least one gain and/or loss are to be recorded for each locus. A cell is considered abnormal if at least one of the identified genetic aberrations identified by a probe set of the present invention is found in that cell. A sample may be considered positive for a gain or loss if the percentage of cells with the respective gain or loss exceeds the cutoff value for any probes used in an assay. Alternatively, two or more genetic aberrations can be required in order to consider the cell abnormal with the effect of increasing specificity. For example, wherein gains are indicative of a melanoma malignancy or precursor lesion, a sample is considered positive if it contains, for example, at least four cells showing gains of at least two or more probe-containing regions.

Probe Combinations and Kits for Use in Diagnostic and/or Prognostic Applications The invention includes highly specific and sensitive combinations of probes that can be used to detect melanoma and kits for use in diagnostic, research, and prognostic applications. These combinations of probes typically have a DFI of less than about 0.29 and often less than about 0.20. Kits include probe sets and can also include reagents such as buffers and the like. The kits may include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

Examples

Probe Selection

CGH Database. The CGH data on which probe selection was based had been acquired at the University of California, San Francisco and has been published previously (Bastian et al, *Am J Pathol.* 163:1765-70, 2003). The data were from 136 primary cutaneous melanoma specimens (63 superficial spreading melanomas (SSM), 30 lentigo maligna melanomas, (LMM), 23 acral-lentiginous (ALM), 4 nodular melanomas (NM), 10 not classifiable (NC), and 6 melanomas arising within a nevus) and 53 benign nevi specimens (19 blue nevi, 7 congenital nevi, 27 Spitz nevi). The genome from the 1p telomere to the 22q telomere (chromosomes X and Y omitted) was divided into 571 bins' according to the Giemsa banding pattern of chromosomes and the CGH ratio corresponding to each bin was interpreted as reflecting chromosomal gain (tumor to reference fluorescence intensity ratio) (ratio >1.2), and loss (ratio <0.8). These thresholds were based on hybridizations of normal DNA versus normal DNA as published previously (Bastian et al, *Cancer Res.*; 58:2170-5, 1998). The sensitivities, specificities, and DFI values to discriminate between nevi and melanomas were calculated at each bin for identifying melanoma by losses or gains. To determine the best combination of bins to discriminate nevi from melanoma, bins were examined in combinations of up to 4, calculating sensitivity, specificity, and DFI value for each combination.

FISH Probe Sets

FISH was performed with eight unique probe sets. Each probe set contained three or four chromosome enumeration probes or locus specific identifiers to centromeres or specific loci of chromosomes (Table 1) that were prevalent in the better performing probe combinations (low DFI values) as determined from the CGH data analysis (see above). The chromsome enumerator probes were included to determine allelic gain or loss of the corresponding locus specific identifiers on those chromosomes (e.g., 9p21 on chromosome 9) or aneusomy of those chromosomes.

TABLE 1

FISH Probes and Gene Target Locations Used for Probe Selection

| Probe Set | Aqua | Green | Orange | Gold | Red |
|---|---|---|---|---|---|
| I | CEP ® 10 | 17q25 (TK1) | 6p25 (RREB1) | | 9p21 (p16) |
| II | CEP ® 9 | 8q24 (MYC) | | 8p22 (LPL) | |
| III | CEP ® 10 | 10q23 (PTEN) | | 1q23 (NTRK1) | |
| IV | CEP ® 6 | CEP ® 7 | | 7q34 (BRAF) | |
| V | CEP ® 8 | CEP ® 9 | | 20q13 | |
| VI | 7q34 (BRAF) | 6p25 (RREB1) | | 20q13 | 9p21 (p16) |

TABLE 1-continued

FISH Probes and Gene Target Locations Used for Probe Selection

| Probe Set | Aqua | Green | Orange | Gold | Red |
|---|---|---|---|---|---|
| VII | 6q23 (MYB) | 6p25 (RREB1) | CEP ® 6 | | |
| VIII | CEP ® 10 | 17q25 (TK1) | | 1q31 (COX2) | 11q13 (CCND1) |

With the exception of the LSI® 17q25 (TK1), LSI® 6p25 (RREB1), LSI® 7q34 (BRAF), LSI® LPL (8p22). LSI® 1q31 (COX2), and LSI® 1q23 (NTRK1) probes, the LSI® and CEP® probes are commercially available from Abbott Molecular Inc. (www.abbottmolecular.com) although LSI® p16 (9p21) and LSI® 20q13 are commercially available only labeled with SpectrumOrange™. Instead of the SpectrumOrange™ label, the nucleic acid starting material was transaminated and then chemically labeled using Texas Red® (trademark of Molecular Probes, Eugene, Oreg.), and 5-(and 6-)-carboxyrhodamine 6G (gold), respectively. The transamination and labeling process is described in Bittner, et al. U.S. Pat. No. 5,491,224, incorporated herein by reference.

The LSI® 1q31 (COX2) probe was made from five BAC clones (Identification Nos. RPCI-11-70N10, RPCI-11-809F11, RPCI-11-104B23, RPCI-11-457L10, RPCI-11-33912). The LSI® 17q25 (TK1) probe was made from two BAC clones (Identification Nos. RPCI11-219g17, RPCI11-153a23). LSI®6p25 (RREB1) was made from two BAC clones (Identification Nos. RPCI11-405o10, RPCI11-61o1). LSI® 7q34 (BRAF) was made from two BAC clones (Identification Nos. RPCI11-837g3, CITD-2516j12). LSI® LPL (8p22) was made from two clones (Identification Nos. 67-o21, CTD-2286-L9). LSI® 1q23 (NTRK1) was made from two BAC clones (Identification Nos. RPCI11-107d16, RPCI11-356j7). Clones were obtained from BAC Pac Resources or Invitrogen. The probes were transaminated and labeled using Texas Red (red), 6-[fluorescein 5-(and-6)-carboxamido]hexanoic acid, succinimidyl ester (green), 5-(and 6-)-carboxyrhodamine 6G, succinimidyl ester (gold) or 5-(and-6)-carboxytetramethylrhodamine, succinimidyl ester.

Study Population and Preparation of Samples for Analysis

The study included specimens of 86 melanomas and 31 benign nevi assembled into microtissue arrays as well as sections from 94 melanoma and 95 benign nevi FFPE skin biopsy specimens.

Paraffin blocks containing tissue biopsy specimens were sectioned at 5 μm thickness and mounted onto SuperFrost Plus® positively charged slides (ThermoShandon, Pittsburgh, Pa.). All slides were baked at 56° C. overnight to fix the tissue onto the slides, and were then stored at room temperature. In preparation for in situ hybridization, array specimen slides were de-paraffinized by soaking in 3 changes of Hemo-De™ Solvent and Clearing Agent (Scientific Safety Solvents, Keller, Tex.) for 5 minutes each, followed by two 1-minute rinses in absolute ethanol. After drying, the specimens were further prepared for in situ hybridization by treatment in 45% formic acid/0.3% $H_2O_2$ for 15 minutes followed by a 3 minute rinse in water. Samples were then immersed in Vysis Pretreatment Solution (Abbott Molecular Inc) at 80° C. for 10 minutes, and rinsed in water for 3 minutes. The slides were then immersed in a solution of Proteinase K (35 μg proteinase K/ml buffer; Abbott Molecular Inc.) at 37° C. for 10 minutes, immersed in 0.01 N HCl for 3 minutes, rinsed in water for 3 minutes, dehydrated in 70%, 85%, and 100% ethanol for 1 minute each, and allowed to dry. In preparation for in situ hybridization, tissue sections were de-paraffinized by soaking in 3 changes of Hemo-De™ Solvent and Clearing Agent (Scientific Safety Solvents, Keller, Tex.) for 5 minutes each, followed by two 1-minute rinses in absolute ethanol. After drying, the specimens were further prepared for in situ hybridization by treatment in 1×SSC pH 6.3 at 80° C. for 35 minutes, and rinsed in water for 3 minutes. The slides were then immersed in a solution of Protease (4 mg protease/ml 0.2 N HCl) at 37° C. for 15 minutes, rinsed in water for 3 minutes, dehydrated in 70%, 85%, and 100% ethanol for 1 minute each, and allowed to dry.

FISH Hybridization

The prepared specimen slides were hybridized with FISH probe solutions in a HYBrite™ automated co-denaturation oven (Abbott Molecular Inc). The slides were placed on the oven surface, probe solution was placed over the tissue section (typically 10 μl), a coverslip was applied over the probe solution, and the edges of the coverslip were sealed to the slide with rubber cement. The oven co-denaturation/hybridization cycle was set for denaturation at 73° C. for 5 minutes, and hybridization at 37° C. for 16-18 h. After hybridization, the slides were removed from the HYBrite, and the rubber cement was removed. The slides were placed in room-temperature 2×SSC (SSC=0.3 M NaCl, 15 mM sodium citrate)/0.3% Nonidet P40 (NP40; Abbott Molecular Inc.) for 2 to 10 minutes to remove the coverslips. The slides were then immersed in 73° C. 2×SSC/0.3% NP40 for 2 minutes for removal of nonspecifically bound probe, and allowed to dry in the dark. DAPI I antifade solution (Abbott Molecular Inc.) was applied to the specimen to allow visualization of the nuclei.

Enumeration of FISH Signals

Slides were analyzed with an epi-fluorescence microscope equipped with single band-pass filters for the DAPI counterstain, SpectrumAqua™, and SpectrumGold™, SpectrumGreen™, SpectrumOrange™, and SpectrumRed™. FISH signal enumeration was performed without knowledge of the patient's clinical or histologic findings. Probe sets I-V were hybridized to tissue microarrays and 40 cells analyzed per specimen. Probe sets VI-VIII were hybridized to specimen sections and 30 cells analyzed per specimen. For specimens with low cellularity, a minimum of 20 nuclei was required for inclusion in the data analysis.

Analysis of Enumeration Data

The FISH number of signals recorded for each cell nucleus within a specimen can be used to classify the corresponding loci as normal (2 signals for loci on autosomes), abnormal due to loss (1 or 0 signals), or abnormal due to gain (greater than 2 signals). Several parameters were defined as measures of abnormal locus gains and losses within a specimen:

Parameters Based on Percentages of Cells Enumerated within a Specimen:

% Gain: 1) for a single locus, % Gain is the percentage of cells with >2 signals corresponding to that locus.

2) for gain of one locus (locus 1) relative to another locus (locus 2), Gain is the percentage of cells with more locus 1 signals than locus 2 signals.

% Loss: 1) for a single locus, % Loss is the percentage of cells with <2 signals corresponding to that locus.

2) for loss of one locus (locus 1) relative to another locus (locus 2), e.g., MYB/CEP 6, Loss is the percentage of cells with fewer locus 1 (e.g., MYB) signals than locus 2 (e.g., CEP 6) signals.

% Abnormal: 1) for a single locus, % Abnormal is the percentage of cells with >2 signals or <2 signals corresponding to that locus.

2) for abnormal balance between two loci (locus 1 and locus 2),

Abnormal is the percentage of cells for which the number of locus 1 signals does not equal the number of locus 2 signals. Parameters Based on Averages Over all Cells Enumerated within a Single Specimen:

average locus copy number: For a single locus, average copy number is the number of signals corresponding to that locus summed over all cells enumerated, divided by number of cells enumerated.

average locus ratio: For a ratio of two loci (locus 1/locus 2), e.g., MYB/CEP 6 shown in Table 6, average locus ratio is the number of locus 1 (e.g., MYB) signals summed over all cells enumerated, divided by number of locus 2, (e.g., CEP 6) signals summed over all cells enumerated.

The values of the above five parameters were tabulated for each locus and relevant locus pairs (e.g., loci on the same chromosome such as 6q23 (MYB) and CEP 6) for each specimen, and the means (x) and standard deviations (s) of each parameter were calculated for the nevi and melanoma specimen groups, excluding specimens of insufficient signal quality for enumeration.

The discriminate value (DV), defined as $(x_1-x_2)^2/(s_1^2+s_2^2)$ was used as a measure of the ability of a specific locus aberration, measured by one of the five parameters above, to distinguish between a sample from the group of patients having melanoma and a sample from the group of patients not exhibiting melanoma. In this formula, x1 and s1 refer to the mean (x) and standard deviation (s) of a specific locus parameter for the melanoma specimen group, and x2 and s2 refer to the mean and standard deviation of that parameter for the benign nevi specimen group. Larger DV values are indicative of a greater ability to distinguish between the two groups of patients. As another measure of discrimination, the Student's t-test was used to compare the values measured for each parameter between the nevi and melanoma specimen groups in order to determine if the differences between the two groups were statistically significant (probabilities <0.05 were considered significant).

Sensitivities and specificities were calculated by applying cutoffs to the various locus parameters for each of the 17 loci. For the % Gain, % Loss, and % Abnormal parameters, a specimen was considered positive for a particular locus if the value of that parameter exceeded the cutoff value. For the average locus copy number and average locus ratio parameters, cutoff values could be applied to distinguish: 1) aberrantly high copy number or ratio, (denoted as r-gain in Table 6), for which parameter values greater than the cutoff value indicated a specimen was positive, 2) aberrantly low copy number or ratio, (denoted by r-loss in Table 6), or 3), for which parameter values less than the cutoff value indicated a specimen was positive, or 3) both conditions 1) and 2). Note that cutoffs values for 1) and 2) may be different.

The sensitivity for detecting specimens with a particular diagnosis was equal to the fraction of specimens in that group that were positive. Specimens that did not provide at least 20 cells with FISH signals of sufficient quality for counting were excluded from the calculation. Specificity, relative to a control group, was calculated as one minus the fraction of the control group specimens that were positive using the same criteria (false positives). For single probes, sensitivity, specificity, and DFI were calculated for cut-off values between 0 and 100% abnormal cells, at 1% increments. The parameter 'distance from ideal' (DFI), which incorporates both sensitivity and specificity, was used to assess the relative performance of each probe or combination of probes.

For combinations of probes cutoffs were applied by two different methods that allowed each locus, as measured by the parameter selected for that locus, to have a different cutoff value. If any of the loci targeted by the probe combination were positive for the respective cutoff, then the specimen was considered positive. Permutation analysis of individual cut-off values between 0 and 100% abnormal cells at 1% increments was not practical for combinations of three or more probes (due to the excessive computation time required), so cut-offs based on the means and standard deviations of the locus parameters for the benign nevi specimen group were calculated first. Cut-offs were generated as x+n*s, where x and s are the mean and standard deviation for a particular locus-specific parameter in the nevi specimen group and n is a multiplier typically ranging from −1 to 3 in increments of 0.1. For probe combinations the cut-off values were calculated using the respective x and s for each probe and parameter in the combination, but for the same value of n. In order to identify the best cutoff values for discriminating between malignancy and benign specimens, cutoff values were calculated for the lowest value of n (e.g., −1), sensitivity, specificity, and DFI values were then calculated based on those cutoffs, n was incremented (e.g., by 0.1), and the calculations were repeated until a maximum value of n (e.g., 3) was reached This procedure provided cut-off values adjusted to each probe based on the level of abnormality and extent of variation in the nevi group. To a first approximation, basing cut-offs on x and common multiples of s establishes a similar specificity relative to the nevi group for each probe and parameter in the combination for each value of n (assuming a normal distribution of parameter values). Probes and probe combinations at each cut-off or set of cut-off values were sorted from lowest to highest DFI in order to identify the better performing probe combinations. Optimal cut-off values for top performing probe combinations (lowest DFI values) were further refined by a second method. By this method cutoffs were independently varied in small increments over a reduced range of cutoffs flanking the optimal cutoffs established by the first method.

Probe complementation was evaluated by calculating sensitivity, specificity, and DFI values for all possible probe combinations up to combinations of four probes, over a range of cutoffs as described above. Each probe was also examined using the five different parameters for measuring aberrations. The relevant parameters examined are included in Tables 2 through 6. Two probes complement one another if a lower DFI value can be achieved for the two probes collectively, than for either probe individually. Typically, only probes providing p-values less than 0.05 in the discrimination analysis (Table 3) were utilized in these calculations in order to reduce the likelihood that low DFI values would result from the combination of random events, and to reduce the computation time. Receiver Operator Characteristics (ROC) graphs were generated by plotting sensitivity versus 1—specificity for a particular probe and parameter or probe combination over the range of cutoff values examined (see above). Since independently varied cut-off values in probe combinations generates multiple sensitivity values for each specificity value, only the highest sensitivity value at each specificity value was plotted, representing the optimal combination of cut-off values for each specificity. Relative performance of a probe or combination of probes can be assessed from these curves by the areas under the curves (better performance indicated by larger areas) or by the distance of closest approach to the point (0, 1) on the graph (100% specificity, 100% sensitivity). Notice that the distance of any point on the curves to the point (0, 1) is equal to the DFI value, and probe combinations with lower DFI values perform better than those with higher DFI values. The cut-offs associated with the lowest DFI value for a particular probe combination are the optimal cutoffs for that combination. However, depending upon the application, points on the ROC curves with somewhat lower DFI values may be selected, after considering the relative clinical importance of sensitivity and specificity. For example, a point on the curve with a slightly higher sensitivity but lower specificity and higher DFI may be chosen over another point on the curve that has a lower sensitivity and higher specificity and lower DFI if it is more important to identify as many cancers as possible, at the expense of a higher false positive rate.

Results

CGH Database Analysis and Selection of Probes for FISH. CGH data were used to identify genetic loci for FISH probe development. The first step in identifying loci was to calculate the sensitivity, specificity, and DFI value at each of the 571 bins across the genome from 1p through 22q with respect to the 136 melanoma specimens and 56 benign nevi specimens. Specificities were 100% at nearly all loci, so only the sensitivities are plotted versus bin number in FIG. 1 parts A (losses), B (gains), and C (amplifications). Loci with highest sensitivities for detecting melanoma include 1p21, 3q29, 6q25.3, 8p23, 9p21, 9q21.1, 10p15, 10q23.3, 11q25, 13q34, 16q24, and 17pter for loss; 1q22, 3p21.3, 6p25.3, 7p21, 7q33, 8q24.2, 15q26, 17q25, and 20q13.3 for gain; and 5p15.3, 11q13.2, and 22q13.1 for amplification. Regions of gain and loss were often broad, at times including whole chromosomes or chromosome arms, indicating FISH probe placement would not be critical, i.e., FISH probes in neighboring bands should usually yield similar efficiency for detecting abnormality.

Centromere status was assessed from the status of non-repetitive sequences flanking the centromere. Centromeres predicted to have high sensitivities for detecting melanoma based on the CGH data included centromeres 3, 6, 9, and 10 for losses, and centromeres 1, 6, 7, 8, and 20 for gains.

The second step in identifying loci for FISH probe development was to examine the ability of different loci to complement one another for detecting malignancy (i.e. sensitivity of combined loci is greater than individual sensitivities of the loci). To this end, sensitivities, specificities and DFI values were calculated for all possible combinations of two, three, and four of the loci listed above. Table 7 shows sensitivities and DFI values for loci and locus combinations with lowest DFI values for the 136 melanoma specimens in the CGH database. For single loci, sensitivities and DFI values are listed for imbalance (gain, loss, or amplification), gain, loss, or amplification. For locus combinations, only the sensitivities and DFI values for imbalance are listed. The individual loci and combinations of loci with the lowest DFI values (FISH) are listed in Table 6 ordered from lowest to highest DFI values. The 14 loci appearing most commonly in the combinations with the lowest DFI values were selected for evaluation by FISH on TMA and include the probe sets I-V in Table 1. Upon analysis of the 14 loci, a subset of the FISH probes was assessed on tissue sections of individual melanocytic tumors (probe set VI). Additional combinations off new probes were also tested on such sections (Probe set VII-VIII; Table 1) to identify loci that complemented one another for detecting malignancy.

Discrimination Analysis

The ability of each FISH probe to discriminate between the group of patients having melanoma and patients having a benign nevus was initially examined by comparing the means and standard deviations of the different parameters for each locus tested between the benign nevi specimen group and the melanoma specimen group. For the tissue microarray hybridizations and for each locus or locus ratio, Table 2 lists the relevant data for the benign nevi specimen group, including the number of specimens evaluated (N), the means of the percent of cells with gain (% Gain) or loss (% Loss), the average locus copy number (single loci) or average locus ratio (ratios of 2 loci), and the corresponding standard deviations. Means and standard deviations were calculated for the melanoma specimen group and are listed in Table 3 for the tissue microarray. Table 3 also lists DVs and p-values, quantities that reflect the ability of particular probes or probe ratios to differentiate between melanoma and normal specimens. The DVs and p-values were consistent in that lower p-values were accompanied by higher DVs. Entries of NA in Table 3 for DV and p-values indicate that the mean of the melanoma group was lower than that of the benign nevi group.

The p-values listed in Table 3 indicate that gains of centromere 8, centromere 9, 1q23, 6p25, 7q34, 17q25, and 20q13 loci, and gain of 7q34 relative to centromere 7 occur in a significantly higher percentage of cells in melanoma specimens than in normal specimens. In addition, loss of the 6p25, 8p22, 8q24, 9p21, 17q25, centromere 6, and centromere 10 loci, and loss of 10q23 (identified using PTEN probe) relative to centromere 10, occur in a significantly higher percentage of cells for melanoma specimens than for normal specimens. Based on DV, the gain of 20q13 and centromere 6 loci showed the greatest level of discrimination between melanoma and nevi, both having DV>1. Likewise, the loss of 9p21, centromere 6, and 17q25 loci showed DV>1.

Based on the data in Table 3, a subset of probes was hybridized to entire tissue sections and analyzed in the same manner using DVs and p-values to confirm the data collected on tissue microarrays. As seen in Table 5, probes selected based upon cells with gain from the tissue microarray data have a similar performance. Several new probes were analyzed on tissue sections (probe sets VII and VIII; Table 1). Means and standard deviations were calculated for melanoma and are listed in Table 5 for the sections. Table 5 also lists DVs and p-values, quantities that reflect the ability of particular probes or probe ratios to differentiate between melanoma and normal specimens. The DVs and p-values were consistent in that lower p-values were accompanied by higher DVs.

The p-values listed in Table 5 indicate that gains of 1q31, 6p25, 6q23, 7q34, 9p21, 11q13, 17q25, 20q13, and relative gain of 6q23 to centromere 6 occur in a significantly higher percentage of cells for melanoma specimens than for normal specimens. Based on the DV, gain of 6p25 showed the greatest level of discrimination between melanoma and nevi, having a DV=0.7.

Single Probe Sensitivities, Specificities, and DFI Values

Sensitivities, specificities, and DFI values were calculated for individual probes hybridized to sections over a range of cut-off values and are listed at the top of Table 6. For melanoma versus nevi, the best DFI values (i.e. lowest DFI values) were obtained for 6p25, 1q31, 7q34, and 20q13 in order from lowest to highest DFI (Table 6). Of these probes, gain of 6p25 was consistently identified as highest performing by the different methods of assessing single probe performance including DV values, p-values from Student's t-test comparisons and 2-tail Fisher's exact test, and DFI values.

Complementation Analysis

In order to determine which probes work best in combination, complementation analysis was performed. Sensitivities, specificities, and DFI values for discriminating melanoma from benign nevi were calculated for all possible probe combinations of 1 to 4 probes. Combinations of as many as 4 probes were analyzed, as four probes are easily combined into a multicolor probe set suitable for viewing through the microscope (visible light emitting labels). Resulting data for top performing probe combinations are listed in Table 6.

Receiver Operator Curves

ROC plots were generated using sensitivities and specificities calculated over the range of cutoff value tested. The ROC curves for a few examples of better performing probe combinations, as judged by lower DFI values in Table 6, are plotted in FIGS. 2A, 2B, and 2C. ROC curves in FIGS. 2A, 2B, and 2C illustrate the relationships between sensitivity and specificity for detecting melanoma specimens relative to the collective group of nevi specimens using probes that detect both loss and gain of loci. ROC curves for the 4 best performing single probes are plotted in order to show improvements (complementation) afforded by combinations of probes (FIG. 2C). The entries in Table 6 correspond to the point on each curve that lies closest to the top left corner of the plot, (0,1). From these plots, or the data in Table 6, it can be seen that gain of 6p25 is complemented by CEP®10 deletion (0 signals/cell), gain of 11q13, or gain of 6q23 for discriminating between melanoma and benign nevi. Since a single probe could provide a DFI as low as 0.2905 (6p25 gain), probe combinations should desirably provide DFI<0.2905 to be worth the added expense of including additional probes in the assay, and the added time required to enumerate the probes. The ROC curves in FIG. 2B representing two-probe combinations can each provide DFI<0.2905, while the three-probe combinations can provide a DFI<0.2622 (FIG. 2B), and the four-probe combination can provide a DFI<0.1937 (FIG. 2C).

The best overall probe combination is seen in FIG. 2C. The ROC curves show that 6p25 gain is complemented by the ratio for 6q23 to centromere 6 (compare ROC curve for the 6p25 gain alone in FIG. 2A and the ROC curve for 6p25 in combination with the ratio for 6q23 to centromere 6 in FIG. 2B), and 6p25 gain combined with the ratio for 6q23 to centromere 6 are further complemented by 17q25 gain (FIG. 2C). The corresponding ROC curve has a DFI value=0.1127 with a sensitivity of 91% and a specificity of 93%. The next best performing probe set in FIG. 2C is the set of 6p25, the ratio of 6q23 to centromere 6, and 11q13 gain. The corresponding ROC curve has a DFI=0.1257 with a sensitivity of 88% and specificity of 97% (Table 6).

As measurements of locus loss can be complicated by truncation artifacts (paraffin sections) and signal overlaps (any specimen preparation), probe combinations that only rely on the measurement of locus gain were also evaluated. The data for the four probe set of all gains including probes 6p25, 6q23, ratio for 6q23 to centromore 6, and 17q25 are included in Table 6 and an example ROC curve is plotted in FIG. 2C. The corresponding ROC curve has a DFI=0.1257 with a sensitivity of 88% and specificity of 97% (Table 6).

Melanoma Detection

The four-color probe sets 6p25, 17q25, 6q23, and CEP® 6; and 6p25, 6q23, CEP® 6 and 11q13 described in this probe selection study can be used to assess formalin fixed paraffin embedded skin biopsy samples for the presence of cells that have chromosomal abnormalities consistent with a diagnosis of melanoma. Samples are prepared for FISH hybridization and subject to hybridization with the probe set as described in the probe selection study. Cells from each sample are evaluated by enumerating 20 to 200 sequential cells, as described in the probe selection study. Samples demonstrating percentages of cells with r-gain of 6p25, 6p25 abnormal, gain of 17q25 or a ratio of total number of 6q23 to centromere 6 signals ≥1.1 that are greater than cutoffs of 2.0%, 66%, 14% or 26%, respectively, are considered positive for melanoma. Samples demonstrating percentages of cells with a r-gain of 6p25, 6p25 abnormal, gain of 11q13 or a ratio of total number of 6q23 to centromere 6 signals ≥1.1 that are greater than cutoffs of 2.0, 66%, 13% and 26%, respectively, are considered positive for melanoma. Hybridization patterns for other probe sets useful for detecting melanoma are shown in Table 6.

Additional Probe Sets

Probe sets that can be useful in detecting melanoma can also be selected based on the DFI values, e.g., less than 0.15, from CGH studies, supra.

Thus, other probe combinations that have been found to be useful have two probes where the two probes are:
a) a chromosome 9 enumerator probe and a probe to chromosome subregion 9p21;
b) probes to chromosome subregions 9p21 and 20q13;
c) a chromosome 8 enumerator probe and a probe that target chromosome subregion 9p21;
d) a chromosome 6 enumerator probe and a probe that targets chromosome subregion 20q13;
e) a chromosome 6 enumerator probe and a chromosome 8 enumerator probe;
f) probes to chromosome subregions 20q13 and 6p25;
g) probes to chromosome subregions 9p21 and 6p25;
h) a chromosome 8 enumerator probe and a probe that targets chromosome subregion 6p25;
i) a chromosome 6 enumerator probe and a probe that targets chromosome subregion 9p21;
j) probes that target chromosome subregions 9p21 and 17q25;
k) a chromosome 8 enumerator probe and a probe that target chromosome subregion 20q13;
l) probes that target chromosome subregions 9p21 and 7q34;
m) probes that target chromosome subregions 9p21 and 1q23
n) probes that target chromosome subregions 20q13 and 1q23; and
o) a chromosome 9 enumerator probe and a probe that target chromosome subregion 20q13.

Useful probe combinations having three probes are:
a) probes to the chromosome subregions 20q13, 9p21, and 7q34;

b) a chromosome 9 enumerator probe, a probe that targets chromosomal subregion 20q13, and a probe that targets chromosome subregion 9p21;
c) a chromosome 9 enumerator probe, a chromosome 8 enumerator probe, and a probe that targets chromosome subregion 9p21;
d) a chromosome 9 enumerator probe, a probe that targets chromosomal subregion 7q34, and a probe that targets chromosome subregion 9p21;
e) a chromosome 8 enumerator probe, a probe that targets chromosomal subregion 20q13, and a probe that targets chromosome subregion 6p25;
f) a chromosome 6 enumerator probe, a probe that targets chromosomal subregion 20q13, and a probe that targets chromosome subregion 9p21;
g) a chromosome 6 enumerator probe, a probe that targets chromosomal subregion 20q13, and a probe that targets chromosome subregion 9p21;
h) a chromosome 8 enumerator probe, a chromosome 10 enumerator probe, and a probe that targets chromosome subregion 9p21;
i) a chromosome 8 enumerator probe, a probe that targets chromosomal subregion 6p25, and a probe that targets chromosome subregion 9p21; and
j) three probes target chromosome subregions 9p21, 6p25, and 7q34.

Useful probe combinations having four probes are:
a) probes to chromosome subregions 9p21, 6p25, 7q34, and 20q13;
b) probes to chromosome subregions 1q23, 6p25, 7q34, and 20q13;
c) a chromosome 6 enumerator probe, a probe that targets chromosome subregion 9p21, a probes that targets chromosome subregion 20q13, and a probe that targets chromosome subregions 7q34; and
d) a chromosome 10 enumerator probe, a probe that targets chromosome subregion 9p21, a probe that targets chromosome subregion 20q13, and a probe that targets chromosome subregions 7q34.

Thus, probe combinations of at least two probes include:
a) a chromosome 9 enumerator probe and a probe to chromosome region 9p;
b) a probe that targets chromosome region 9p and a probe that targets chromosome region 20q;
c) a chromosome 8 enumerator probe and a probe that targets chromosome region 9p;
d) a chromosome 6 enumerator probe and a probe that targets chromosome region 20q;
e) a probe that targets chromosome region 20q and a probe that targets chromosome region 6p;
f) a probe that targets chromosome region 9p and a probe that targets chromosome region 6p;
g) a chromosome 8 enumerator probe and a probe that targets chromosome region 6p;
h) a chromosome 6 enumerator probe and a probe that targets chromosome region 9p;
i) a probe that targets chromosome region 9p and a probe that targets chromosome region 17q;
j) a chromosome 8 enumerator probe and a probe that target chromosome region 20q;
k) a probe that targets chromosome region 9p and a probe that targets chromosome region 7q;
l) a probe that targets chromosome region 9p and a probe that targets chromosome region 1 q;
m) a probe that targets chromosome region 20q and a probe that targets chromosome region 1q; and
n) a chromosome 9 enumerator probe and a probe that target chromosome region 20q.

Probe combinations of at least three probes include:
a) a probe that targets chromosome region 20q, a probe that targets chromosome region 9p, and a probe that targets chromosome region 7q;
b) a chromosome 9 enumerator probe, a probe that targets chromosomal b region 20q, and a probe that targets chromosome region 9p;
c) a chromosome 9 enumerator probe, a chromosome 8 enumerator probe, and a probe that targets chromosome region 9p;
d) a chromosome 9 enumerator probe, a probe that targets chromosomal region 7q, and a probe that targets chromosome region 9p;
e) a chromosome 8 enumerator probe, a probe that targets chromosomal region 20q, and a probe that targets chromosome region 6p;
f) a chromosome 6 enumerator probe, a probe that targets chromosomal region 20q, and a probe that targets chromosome region 9p;
g) a chromosome 6 enumerator probe, a probe that targets chromosomal region 20q, and a probe that targets chromosome region 9p;
h) a chromosome 8 enumerator probe, a chromosome 10 enumerator probe, and a probe that targets chromosome region 9p;
i) a chromosome 8 enumerator probe, a probe that targets chromosomal region 6p, and a probe that targets chromosome region 9p; and
j) a probe that targets chromosome region 9p, a probe that targets chromosome region 6p, and a probe that targets chromosome region 7q.

Probe combinations of at least four probes include:
a) a probe that targets chromosome region 9p, a probe that targets chromosome region 6p, a probe that targets chromosome region 7q, and a probe that targets chromosome region 20q;
b) a probe that targets chromosome region 1 q, a probe that targets chromosome region 6p, a probe that targets chromosome region 7q, and a probe that targets chromosome region 20q;
c) a chromosome 6 enumerator probe, a probe that targets chromosome region 9p, a probe that targets chromosome region 20q, and a probe that targets chromosome region 7q; and
d) a chromosome 10 enumerator probe, a probe that targets chromosome region 9p, a probe that targets chromosome region 20q, and a probe that targets chromosome region 7q.

Other Embodiments

It is to be understood that, while the invention has been described in conjunction with the detailed description, thereof, the foregoing description is intended to illustrate and not limit the scope of the invention. Other aspects, advantages, and modifications of the invention are within the scope of the claims set forth below.

All publications, patents, and patent applications cited in this specification are herein incorporated by reference as if each individual publication or patent application were specifically and individually indicated to be incorporated by reference.

TABLE 2

Nevus specimen set on tissue microarray (sd = standard deviation, DV = discriminate value)

| PROBE | N | Cells with gain Ave. % cells with gain | Cells with gain sd % cells gain | Cells with loss Ave. % cells with loss | Cells with loss sd % cells with loss | Probe signals/cell or Probe 1/Probe 2 Ave. locus copy number or ratio | Probe signals/cell or Probe 1/Probe 2 sd copy number of ratio |
|---|---|---|---|---|---|---|---|
| NTRK1 (1q23) | 29 | 4.80 | 6.85 | 36.95 | 20.81 | 1.69 | 0.25 |
| RREB1 (6p25) | 31 | 3.20 | 5.34 | 30.65 | 11.73 | 1.74 | 0.16 |
| CEP 6 | 22 | 8.60 | 7.52 | 49.57 | 19.51 | 1.61 | 0.28 |
| BRAF (7q34) | 22 | 6.16 | 5.42 | 49.34 | 18.18 | 1.59 | 0.22 |
| CEP 7 | 22 | 11.48 | 8.11 | 35.88 | 19.16 | 1.79 | 0.26 |
| LPL (8p22) | 23 | 27.93 | 14.73 | 16.92 | 10.99 | 2.26 | 0.36 |
| MYC (8q24) | 23 | 28.62 | 9.47 | 17.79 | 9.75 | 2.24 | 0.27 |
| CEP 8 | 22 | 0.81 | 2.36 | 50.50 | 19.56 | 1.50 | 0.20 |
| p16 (9p21) | 31 | 3.84 | 4.99 | 33.82 | 10.07 | 1.73 | 0.21 |
| CEP 9 | 22 | 0.84 | 1.84 | 45.53 | 16.69 | 1.55 | 0.17 |
| PTEN (10q23) | 29 | 5.97 | 6.71 | 43.42 | 17.96 | 1.64 | 0.24 |
| CEP 10(probe set 2) | 31 | 3.51 | 2.89 | 42.52 | 10.90 | 1.60 | 0.15 |
| CEP 10(probe set 5) | 29 | 5.95 | 8.05 | 47.58 | 18.23 | 1.61 | 0.28 |
| CEP 10(avg. for set 2 and 5) | 33 | 4.67 | 4.26 | 44.92 | 10.04 | 1.60 | 0.15 |
| TK1 (17q25) | 31 | 3.40 | 6.14 | 29.22 | 10.50 | 1.75 | 0.16 |
| 20q13 | 22 | 1.14 | 3.43 | 47.02 | 24.64 | 1.54 | 0.26 |
| LPL/MYC | 23 | 20.29 | 10.77 | 19.17 | 7.40 | 1.01 | 0.09 |
| PTEN/CEP10 | 29 | 19.13 | 9.72 | 16.05 | 7.16 | 1.03 | 0.11 |
| BRAF/CEP7 | 22 | 7.05 | 6.46 | 25.63 | 7.66 | 0.89 | 0.07 |
| RREB1/CEP6* | 21 | | | | | 1.12 | 0.22 |
| LPL/CEP8* | 18 | | | | | 1.48 | 0.31 |
| MYC/CEP8* | 18 | | | | | 1.49 | 0.24 |
| p16/CEP9* | 22 | | | | | 1.13 | 0.18 |

*ratios are estimates based on average signals per cell for each probe measured in different hybridizations.

TABLE 3

Melanoma cases on tissue microarray (sd = standard deviation, DV = discriminate value)

| PROBE | N | Cells with gain Ave. % cells with gain | Cells with gain sd % cells with gain | Cells with gain DV | Cells with gain p | Cells with loss Ave. % cells with loss | Cells with loss sd % cells with loss | Cells with loss DV | Cells with loss p | Probe signals/cell or Probe 1/Probe 2 Ave. locus copy number or ratio | Probe signals/cell or Probe 1/Probe 2 sd copy number of ratio | Probe signals/cell or Probe 1/Probe 2 DV | Probe signals/cell or Probe 1/Probe 2 p |
|---|---|---|---|---|---|---|---|---|---|---|---|---|---|
| NTRK1 (1q23) | 75 | 19.15 | 17.15 | 0.60 | 0.00 | 30.58 | 14.55 | 0 | NA | 1.97 | 0.40 | 0.34 | 0.00 |
| RREB1 (6p25) | 66 | 16.06 | 17.48 | 0.50 | 0.00 | 42.36 | 17.88 | 0 | 0.00 | 1.88 | 0.91 | 0.02 | 0.24 |
| CEP 6 | 86 | 3.15 | 5.38 | 0.35 | NA | 78.14 | 16.60 | 1 | 0.00 | 1.26 | 0.23 | 0.93 | NA |
| BRAF (7q34) | 86 | 12.98 | 14.78 | 0.19 | 0.00 | 48.14 | 16.83 | 0 | NA | 1.70 | 0.51 | 0.04 | 0.12 |
| CEP 7 | 86 | 15.72 | 13.61 | 0.07 | 0.07 | 39.36 | 14.95 | 0 | 0.44 | 1.81 | 0.32 | 0.00 | 0.82 |
| LPL (8p22) | 39 | 23.09 | 17.05 | 0.05 | NA | 31.71 | 15.32 | 1 | 0.00 | 2.16 | 1.19 | 0.01 | NA |
| MYC (8q24) | 39 | 19.00 | 15.31 | 0.29 | NA | 34.86 | 15.68 | 1 | 0.00 | 1.93 | 0.39 | 0.43 | NA |
| CEP 8 | 84 | 14.52 | 12.62 | 1.14 | 0.00 | 44.07 | 15.80 | 0 | NA | 1.76 | 0.33 | 0.43 | 0.00 |
| p16 (9p21) | 66 | 5.38 | 7.67 | 0.03 | 0.24 | 60.47 | 17.98 | 2 | 0.00 | 1.43 | 0.27 | 0.76 | NA |
| CEP 9 | 84 | 10.62 | 11.30 | 0.73 | 0.00 | 50.65 | 17.78 | 0 | 0.21 | 1.63 | 0.32 | 0.05 | 0.12 |
| PTEN (10q23) | 75 | 7.87 | 9.26 | 0.03 | 0.25 | 42.94 | 16.57 | 0 | NA | 1.67 | 0.26 | 0.01 | 0.57 |
| CEP 10 | 93 | 6.71 | 7.42 | 0.06 | 0.06 | 52.04 | 14.63 | 0 | 0.00 | 1.51 | 0.25 | 0.08 | NA |
| TK1 (17q25) | 66 | 8.16 | 9.52 | 0.18 | 0.00 | 53.74 | 16.88 | 2 | 0.00 | 1.52 | 0.33 | 0.41 | NA |
| 20q13 | 84 | 21.91 | 19.32 | 1.12 | 0.00 | 34.19 | 14.80 | 0 | NA | 2.02 | 0.60 | 0.54 | 0.00 |
| LPL/MYC | 39 | 28.43 | 13.86 | 0.21 | 0.01 | 21.05 | 10.28 | 0 | 0.41 | 1.11 | 0.42 | 0.06 | 0.15 |
| PTEN/CEP10 | 75 | 16.95 | 8.48 | 0.03 | NA | 20.21 | 11.14 | 0 | 0.03 | 0.99 | 0.12 | 0.06 | NA |
| BRAF/CEP7 | 86 | 16.15 | 12.36 | 0.43 | 0.00 | 26.59 | 11.74 | 0 | 0.65 | 0.95 | 0.30 | 0.04 | 0.07 |
| RREB1/CEP6* | 51 | | | | | | | | | 1.55 | 0.81 | 0.26 | 0.00 |
| LPL/CEP8* | 34 | | | | | | | | | 1.14 | 0.20 | 0.82 | NA |
| MYC/CEP8* | 34 | | | | | | | | | 1.11 | 0.24 | 1.25 | NA |
| p16/CEP9* | 55 | | | | | | | | | 0.87 | 0.18 | 1.02 | NA |

TABLE 4

Nevus specimen set on sections

| | | Nevus Specimen Set | | | | | | | |
|---|---|---|---|---|---|---|---|---|---|
| PROBE | Number of specimens | Ave. % cells with gain | S.D. % cells with gain | Ave. % cells with loss | S.D. % cells with loss | Ave. % cells with imbalance | S.D. % cells with imbalance | Ave. ratio | S.D. ratio |
| RREB1 (6p25) | 81 | 8.2922 | 10.4349 | 44.1975 | 13.7617 | 52.4897 | 12.9371 | 1.6226 | 0.2536 |
| BRAF (7q34) | 81 | 4.5268 | 6.5682 | 62.8395 | 15.4592 | 67.3663 | 13.6673 | 1.3554 | 0.2285 |
| 20q13 | 81 | 10.7819 | 11.5413 | 43.9506 | 12.1548 | 54.7325 | 11.2776 | 1.6416 | 0.2811 |
| p16 (9p21) any del | 81 | 5.4733 | 7.9461 | 52.9424 | 15.0422 | 58.4156 | 14.1321 | 1.4572 | 0.2653 |
| p16 (9p21) del (1 signal/cell) | 81 | 5.4733 | 7.9461 | 44.1358 | 13.0679 | 49.6090 | 12.7755 | 1.4572 | 0.2653 |
| p16 (9p21) del (0 signals/cell) | 81 | 5.4733 | 7.9461 | 8.8066 | 6.3532 | 14.2798 | 9.1929 | 1.4572 | 0.2653 |
| RREB1/p16 any del | 81 | 34.8560 | 12.4058 | 23.5597 | 10.7230 | 58.4156 | 11.9777 | 1.1388 | 0.2304 |
| BRAF/p16 any del | 80 | 24.1511 | 10.1229 | 33.0258 | 10.8556 | 57.1769 | 11.6528 | 0.9455 | 0.1836 |
| 20q13/p16 any del | 80 | 24.1667 | 10.1258 | 33.0208 | 10.8600 | 57.1875 | 11.6458 | 1.1457 | 0.2547 |
| RREB1/BRAF | 81 | 39.6296 | 11.0604 | 18.5597 | 8.9704 | 58.1893 | 10.5548 | 1.2140 | 0.1848 |
| RREB1/20q | 81 | 27.9424 | 10.1320 | 29.2387 | 9.4577 | 57.1811 | 11.3855 | 0.9997 | 0.1343 |
| BRAF/20q | 79 | 18.8819 | 8.8301 | 39.1561 | 10.7048 | 58.0380 | 12.1063 | 0.8357 | 0.1200 |
| TK1 (17q25) | 30 | 5.5412 | 5.0317 | 46.9534 | 9.7086 | 52.4946 | 10.0194 | 1.5283 | 0.1508 |
| CCND (11q13) | 30 | 4.3226 | 5.5357 | 43.2903 | 11.8843 | 47.6129 | 12.5514 | 1.5704 | 0.1952 |
| COX2 (1q23) | 30 | 2.8817 | 2.8669 | 60.5771 | 10.0991 | 63.4588 | 9.3219 | 1.2926 | 0.1724 |
| CEP10 any del | 30 | 1.4444 | 2.5795 | 62.6165 | 12.7613 | 64.0609 | 12.1295 | 1.3353 | 0.1365 |
| CEP10 del (1 signal/cell) | 30 | 1.4444 | 2.5795 | 57.3154 | 14.4824 | 58.7599 | 13.6419 | 1.3353 | 0.1365 |
| CEP10 del (0 signals/cell) | 30 | 1.4444 | 2.5795 | 5.3011 | 4.9629 | 6.7455 | 6.2607 | 1.3353 | 0.1365 |
| TK1/CEP10 any del | 30 | 36.1219 | 8.9908 | 21.2473 | 8.9356 | 57.3692 | 8.3119 | 1.1549 | 0.1575 |
| CCND/CEP10 any del | 30 | 37.9068 | 11.4420 | 18.2652 | 10.4954 | 56.1720 | 10.2684 | 1.1874 | 0.1838 |
| COX2/CEP10 any del | 30 | 28.9283 | 7.5494 | 31.0860 | 10.5999 | 60.0143 | 9.2432 | 0.9743 | 0.1356 |
| TK1/CCND | 30 | 26.4588 | 9.5039 | 29.6846 | 8.5423 | 56.1434 | 9.4157 | 0.9863 | 0.1454 |
| TK1/COX2 | 30 | 39.6416 | 7.8529 | 22.2616 | 7.5379 | 61.9032 | 7.4944 | 1.1995 | 0.1755 |
| CCND/COX2 | 30 | 39.1792 | 9.6529 | 20.3728 | 9.7491 | 59.5520 | 10.0786 | 1.2392 | 0.2647 |
| MYB (6q23) | 13 | 10.8974 | 22.8989 | 26.0256 | 12.5377 | 36.9231 | 19.3631 | 1.8795 | 0.3941 |
| CEP 6 | 13 | 12.9487 | 20.0018 | 27.1795 | 11.8514 | 40.1282 | 14.5370 | 1.8795 | 0.3655 |
| MYB/CEP 6 | 13 | 18.3333 | 5.0000 | 17.5641 | 9.7329 | 35.8974 | 9.4432 | 0.9493 | 0.0561 |

TABLE 5

Melanoma specimen set on sections

| | | All Malignancies | | | | | | | | |
|---|---|---|---|---|---|---|---|---|---|---|
| PROBE | No. of specimens | Ave. % cells with gain | S.D. % cells with gain | Discrimate Value - % gain | p % gain | Ave. % cells with loss | S.D. % cells with loss | Discrimate Value - % loss | p % loss | Ave. % cells Abnormal |
| RREB1 (6p25) | 94 | 27.3759 | 19.4419 | 0.7480 | 0.0000 | 30.0000 | 13.3959 | 0.5465 | 0.0000 | 57.3759 |
| BRAF (7q34) | 93 | 14.4086 | 14.8353 | 0.3710 | 0.0000 | 49.3190 | 18.9428 | 0.3058 | 0.0000 | 63.7276 |
| 20q13 | 94 | 22.1631 | 17.8049 | 0.2877 | 0.0000 | 35.1064 | 15.7543 | 0.1976 | 0.0000 | 57.2695 |
| p16 (9p21) any del | 94 | 8.7234 | 10.8768 | 0.0582 | 0.0241 | 56.3120 | 19.6776 | 0.0185 | 0.2017 | 65.0355 |
| p16 (9p21) del (1 signal/cell) | 94 | 8.7234 | 10.8768 | 0.0582 | 0.0241 | 42.6596 | 15.4392 | 0.0053 | 0.4943 | 51.3830 |
| p16 (9p21) del (0 signals/cell) | 94 | 8.7234 | 10.8768 | 0.0582 | 0.0241 | 13.6525 | 13.6001 | 0.1042 | 0.0025 | 22.3759 |
| RREB1/p16 any del | 94 | 52.4468 | 17.9417 | 0.6503 | 0.0000 | 15.9574 | 10.0283 | 0.2681 | 0.0000 | 68.4042 |
| BRAF/p16 any del | 88 | 37.7652 | 19.1567 | 0.3948 | 0.0000 | 27.1212 | 12.7375 | 0.1245 | 0.0014 | 64.8864 |
| 20q13/p16 any del | 93 | 37.9570 | 19.2243 | 0.4028 | 0.0000 | 26.9893 | 12.7600 | 0.1296 | 0.0010 | 64.9462 |
| RREB1/BRAF | 91 | 45.1648 | 15.5576 | 0.0841 | 0.0074 | 19.4872 | 11.2098 | 0.0042 | 0.5480 | 64.6520 |
| RREB1/20q | 93 | 37.3118 | 13.7811 | 0.3000 | 0.0000 | 27.4552 | 14.3826 | 0.0107 | 0.3298 | 64.7670 |
| BRAF/20q | 90 | 24.4815 | 11.9942 | 0.1413 | 0.0006 | 41.4444 | 13.5382 | 0.0176 | 0.2222 | 65.9259 |
| TK1 (17q25) | 28 | 17.5509 | 17.1183 | 0.4531 | 0.0012 | 36.0326 | 13.6046 | 0.4269 | 0.0010 | 53.5835 |
| CCND (11q13) | 28 | 20.0029 | 26.4299 | 0.3372 | 0.0045 | 32.3322 | 15.6338 | 0.3114 | 0.0043 | 52.3351 |
| COX2 (1q31) | 28 | 10.1183 | 12.5577 | 0.3156 | 0.0057 | 48.2324 | 13.7921 | 0.5215 | 0.0003 | 58.3506 |
| CEP10 any del | 28 | 3.8433 | 5.6027 | 0.1513 | 0.0454 | 57.1083 | 12.8267 | 0.0927 | 0.1070 | 60.9516 |
| CEP10 del (1 signal/cell) | 28 | 3.8433 | 5.6027 | 0.1513 | 0.0454 | 49.8174 | 11.7569 | 0.1616 | 0.0343 | 53.6607 |
| CEP10 del (0 signals/cell) | 28 | 3.8433 | 5.6027 | 0.1513 | 0.0454 | 7.2909 | 8.3930 | 0.0416 | 0.2821 | 11.1342 |
| TK1/CEP10 any del | 28 | 43.5521 | 14.4407 | 0.1920 | 0.0239 | 17.6182 | 8.7643 | 0.0841 | 0.1242 | 61.1703 |
| CCND/CEP10 any del | 28 | 49.7590 | 18.2212 | 0.3034 | 0.0051 | 14.8285 | 7.6359 | 0.0701 | 0.1578 | 64.5874 |
| COX2/CEP10 any del | 28 | 35.7275 | 12.3092 | 0.2217 | 0.0156 | 24.5204 | 7.9564 | 0.2454 | 0.0098 | 60.2479 |
| TK1/CCND | 28 | 26.4201 | 15.8924 | 0.0000 | 0.9912 | 35.5192 | 22.2996 | 0.0597 | 0.2028 | 61.9393 |
| TK1/COX2 | 28 | 36.8700 | 15.5970 | 0.0252 | 0.4029 | 23.6260 | 12.4005 | 0.0088 | 0.6181 | 60.4961 |

TABLE 5-continued

| Melanoma specimen set on sections | | | | | | | | | |
|---|---|---|---|---|---|---|---|---|---|
| CCND/COX2 | 28 | 42.9226 | 21.8386 | 0.0246 | 0.4096 | 20.9330 | 12.9700 | 0.0012 | 0.8540 | 63.8556 |
| MYB (6q23) | 13 | 31.5608 | 35.3830 | 0.2404 | 0.0920 | 15 | 14.5688 | 0.3214 | 0.0523 | 47 |
| CEP 6 | 13 | 25.2285 | 33.9744 | 0.0970 | 0.2751 | 22.8986 | 14.4728 | 0.0524 | 0.4177 | 48.1271 |
| MYB/CEP 6 | 13 | 28.1828 | 13.6087 | 0.4615 | 0.0269 | 16.8785 | 12.6174 | 0.0019 | 0.8781 | 45.0613 |

| | All Malignancies | | | | | | |
|---|---|---|---|---|---|---|---|
| PROBE | S.D. % cells Abnormal | Discrimate Value - % Abnormal | p % Abnormal | Ave. locus copy number or ratio | S.D. copy number or ratio | Discriminate Value copy number or ratio | p ratio |
| RREB1 (6p25) | 13.9283 | 0.0661 | 0.0173 | 2.1238 | 0.5225 | 0.7444 | 0.0000 |
| BRAF (7q34) | 12.1370 | 0.0396 | 0.0669 | 1.6756 | 0.4600 | 0.3888 | 0.0000 |
| 20q13 | 12.4910 | 0.0227 | 0.1599 | 1.9702 | 0.5375 | 0.2936 | 0.0000 |
| p16 (9p21) any del | 14.2327 | 0.1089 | 0.0024 | 1.4220 | 0.4224 | 0.0050 | 0.5042 |
| p16 (9p21) del (1 signal/cell) | 12.6000 | 0.0098 | 0.3580 | 1.4220 | 0.4224 | 0.0050 | 0.5042 |
| p16 (9p21) del (0 signals/cell) | 14.0797 | 0.2318 | 0.0000 | 1.4220 | 0.4224 | 0.0050 | 0.5042 |
| RREB1/p16 any del | 14.0891 | 0.2918 | 0.0000 | 1.7599 | 1.6497 | 0.1390 | 0.0005 |
| BRAF/p16 any del | 11.7330 | 0.2174 | 0.0000 | 1.4277 | 1.8232 | 0.0692 | 0.0155 |
| 20q13/p16 any del | 11.5847 | 0.2231 | 0.0000 | 1.7361 | 2.8371 | 0.0430 | 0.0487 |
| RREB1/BRAF | 12.2915 | 0.1591 | 0.0003 | 1.2979 | 0.2949 | 0.0582 | 0.0251 |
| RREB1/20q | 11.5198 | 0.2194 | 0.0000 | 1.1116 | 0.2500 | 0.1553 | 0.0003 |
| BRAF/20q | 11.2711 | 0.2274 | 0.0000 | 0.8771 | 0.2166 | 0.0279 | 0.1212 |
| TK1 (17q25) | 16.4147 | 0.0032 | 0.7638 | 1.8624 | 0.4326 | 0.5317 | 0.0005 |
| CCND (11q13) | 19.7416 | 0.0407 | 0.2865 | 2.5904 | 2.9406 | 0.1198 | 0.0780 |
| COX2 (1q31) | 10.7742 | 0.1286 | 0.0596 | 1.5906 | 0.3159 | 0.6854 | 0.0001 |
| CEP10 any del | 12.3963 | 0.0321 | 0.3390 | 1.4004 | 0.2094 | 0.0679 | 0.1705 |
| CEP10 del (1 signal/cell) | 10.7429 | 0.0862 | 0.1183 | 1.4004 | 0.2094 | 0.0679 | 0.1705 |
| CEP10 del (0 signals/cell) | 10.6674 | 0.1259 | 0.0650 | 1.4004 | 0.2094 | 0.0679 | 0.1705 |
| TK1/CEP10 any del | 13.8627 | 0.0553 | 0.2160 | 1.3550 | 0.3886 | 0.2279 | 0.0157 |
| CCND/CEP10 any del | 13.5475 | 0.2451 | 0.0107 | 1.7550 | 1.5584 | 0.1308 | 0.0659 |
| COX2/CEP10 any del | 12.2438 | 0.0002 | 0.9353 | 1.1439 | 0.1974 | 0.5009 | 0.0004 |
| TK1/CCND | 18.2061 | 0.0800 | 0.1397 | 0.9729 | 0.3676 | 0.0012 | 0.8576 |
| TK1/COX2 | 15.3093 | 0.0068 | 0.6626 | 1.2017 | 0.3441 | 0.0000 | 0.9768 |
| CCND/COX2 | 15.8538 | 0.0525 | 0.2273 | 1.5917 | 1.4590 | 0.0565 | 0.2181 |
| MYB (6q23) | 29.2514 | 0.0775 | 0.3270 | 2.3313 | 0.6907 | 0.3229 | 0.0545 |
| CEP 6 | 25.3944 | 0.0747 | 0.3366 | 2.1713 | 0.7598 | 0.1198 | 0.2286 |
| MYB/CEP 6 | 19.2473 | 0.1827 | 0.1412 | 0.9252 | 0.1435 | 0.0245 | 0.5804 |

TABLE 6

| PROBE 1 | Pobe 1 Parameter | PROBE 2 | Probe 2 parameter | PROBE 3 | Probe 3 Parameter | PROBE 4 |
|---|---|---|---|---|---|---|
| RREB1 (6p25) | r-gain or % gain | | | | | |
| RREB1 (6p25) | r-gain or % abnormal | | | | | |
| RREB1 (6p25) | r-gain | | | | | |
| COX2 (1q31) | r-gain | | | | | |
| BRAF (7q34) | % gain | | | | | |
| 20q13 | % gain | | | | | |
| RREB1 (6p25) | r-gain or % abnormal | CCND (11q13) | % gain | | | |
| MYB(6q23) | r-gain | RREB1 (6p25) | r-gain or % abnormal | | | |
| CEP10 | % loss (no signals) | RREB1 (6p25) | r-gain or % abnormal | | | |
| RREB1 (6p25) | r-gain or % abnormal | CEP10 | % abnormal (0 or >2 signals) | | | |
| CEP10 | % loss (no signals) | RREB1 (6p25) | r-gain | | | |
| MYB(6q23) | r-gain | RREB1 (6p25) | r-gain | | | |
| 20q13 | % gain | RREB1 (6p25) | % gain | | | |
| RREB1 (6p25) | r-gain | CCND (11q13) | % gain | | | |
| CEP10 | % loss (no signals) | COX2 (1q31) | r-gain | | | |
| RREB1 (6p25) | r-gain | COX2 (1q31) | r-gain | | | |
| COX2 (1q31) | r-gain | CEP10 | % abnormal (0 or >2 signals) | | | |
| MYB(6q23) | r-gain | COX2 (1q31) | r-gain | | | |
| BRAF (7q34) | % gain | RREB1 (6p25) | % gain | | | |
| MYB(6q23) | % gain | COX2 (1q31) | r-gain | | | |
| MYB(6q23)/CEP 6 | % gain | RREB1 (6p25) | r-gain or % abnormal | | | |

TABLE 6-continued

| | | | | | | | |
|---|---|---|---|---|---|---|---|
| MYB(6q23)/CEP 6 | % gain | RREB1 (6p25) | % abnormal or % gain | | | | |
| BRAF (7q34) | r-gain | RREB1 (6p25) | r-gain or % abnormal | TK1 (17q25) | % gain | | |
| 20q13 | r-gain | RREB1 (6p25) | r-gain or % abnormal | TK1 (17q25) | % gain | | |
| RREB1 (6p25) | % gain | COX2 (1q31) | % gain | TK1 (17q25) | % gain | | |
| MYB(6q23)/CEP 6 | % gain | MYB(6q23) | r-gain | RREB1 (6p25) | % gain | | |
| 20q13 | r-gain | RREB1 (6p25) | r-gain or % abnormal | CCND (11q13) | % gain | | |
| CCND (11q13)/CEP10 | % gain | RREB1 (6p25) | % gain | | | | |
| CEP10 | % loss (no signals) or % gain | RREB1 (6p25) | % gain | TK1 (17q25) | % gain | | |
| 20q13 | r-gain | MYB(6q23) | r-gain | RREB1 (6p25) | r-gain or % abnormal | | |
| BRAF (7q34) | r-gain or % gain | RREB1 (6p25) | r-gain | TK1 (17q25) | % gain | | |
| 20q13 | r-gain or % gain | RREB1 (6p25) | r-gain | TK1 (17q25) | % gain | | |
| RREB1 (6p25) | r-gain | COX2 (1q31) | r-gain or % gain | TK1 (17q25) | % gain | | |
| RREB1 (6p25) | % gain | CCND (11q13) | % gain | TK1 (17q25) | % gain | | |
| RREB1 (6p25) | % gain | CEP10 | % gain | TK1 (17q25) | % gain | | |
| CCND/CEP10 any del | r-gain or % abnormal | CEP10 | % loss (no signals) | RREB1 (6p25) | r-gain | | |
| BRAF (7q34) | r-gain | CEP10 homo del | % loss (no signals) | RREB1 (6p25) | r-gain or % abnormal | | |
| 20q13 | r-gain | CEP10 homo del | % loss (no signals) | RREB1 (6p25) | r-gain or % abnormal | | |
| CEP10 | % loss (no signals) | COX2 (1q31) | r-gain | RREB1 (6p25) | % gain | | |
| COX2 (1q31) | r-gain | CEP10 | % abnormal (0 or >2 signals) | RREB1 (6p25) | % gain | | |
| CEP10 | % loss (no signals) | RREB1 (6p25) | r-gain | CCND (11q13) | % gain | | |
| RREB1 (6p25) | r-gain | CEP10 | % abnormal (0 or >2 signals) | CCND (11q13) | % gain | | |
| RREB1 (6p25) | r-gain | COX2 (1q31) | r-gain | RREB1 (6p25) | % abnormal | CCND (11q13) | |
| COX2/CEP10 | % gain | RREB1 (6p25) | % gain | | | | |
| CCND/CEP10 | % gain | CEP10 | % loss (no signals) | RREB1 (6p25) | r-gain | | |
| COX2 (1q31) | % gain | CCND (11q13) | % gain | TK1 (17q25) | % gain | | |
| RREB1 (6p25) | % gain | COX2 (1q31) | % gain | CCND (11q13) | % gain | | |
| CEP10 | % loss (no signals) | RREB1 (6p25) | % gain | COX2 (1q31) | % gain | | |
| MYB(6q23) | r-gain | RREB1 (6p25) | r-gain | CCND (11q13) | % gain | | |
| COX2 (1q23) | r-gain | RREB1 (6p25) | % gain | CCND (11q13) | % gain | | |
| CEP10 | % abnormal (0 or >2 signals) | RREB1 (6p25) | % gain | CCND (11q13) | % gain | | |
| 20q13 | % gain | BRAF (7q34) | % gain | RREB1 (6p25) | % gain | | |
| MYB(6q23)/CEP 6 | % gain | RREB1 (6p25) | r-gain or % abnormal | TK1 (17q25) | % gain | | |
| MYB(6q23)/CEP 6 | % gain | RREB1 (6p25) | r-gain or % abnormal | CCND (11q13) | % gain | | |
| MYB(6q23)/CEP 6 | % gain | MYB(6q23) | r-gain | RREB1 (6p25) | % gain | TK1 (17q25) | |
| MYB(6q23)/CEP 6 | % gain | CEP10 | signals) | RREB1 (6p25) | % gain | | |
| MYB(6q23)/CEP 6 | % gain | RREB1 (6p25) | r-gain or % abnormal | CEP10 | % abnormal (0 or >2 signals) | | |
| 20q13 | r-gain | MYB(6q23)/CEP 6 | % gain | RREB1 (6p25) | r-gain or % abnormal | | |
| BRAF (7q34) | r-gain | MYB(6q23)/CEP 6 | % gain | RREB1 (6p25) | r-gain | | |
| BRAF (7q34) | r-gain | COX2 (1q31) | r-gain | RREB1 (6p25) | % gain | TK1 (17q25) | |
| 20q13 | r-gain | COX2 (1q31) | r-gain | RREB1 (6p25) | % gain | TK1 (17q25) | |
| RREB1 (6p25) | % gain | COX2 (1q31) | % gain | CCND (11q13) | % gain | TK1 (17q25) | |
| 20q13 | r-gain | MYB(6q23)/CEP 6 | % gain | MYB(6q23) | r-gain | RREB1 (6p25) | |
| RREB1 (6p25) | % gain | COX2 (1q31) | % gain | CEP10 any del | % gain | TK1 (17q25) | |
| BRAF (7q34) | r-gain | MYB(6q23) | r-gain | RREB1 (6p25) | r-gain | TK1 (17q25) | |
| 20q13 | r-gain | MYB(6q23) | r-gain | RREB1 (6p25) | r-gain | TK1 (17q25) | |
| CCND/CEP10 | r-gain | BRAF(7q34) | r-gain | RREB1 (6p25) | r-gain or % abnormal | | |
| CCND/CEP10 | r-gain | 20q13 | r-gain | RREB1 (6p25) | r-gain or % abnormal | | |
| BRAF (7q34) | r-gain | MYB(6q23)/CEP 6 | % gain | MYB(6q23) | r-gain | RREB1 (6p25) | |
| BRAF (7q34) | r-gain or % gain | MYB(6q23)/CEP 6 | % gain | RREB1 (6p25) | % gain | | |
| 20q13 | r-gain or % gain | MYB(6q23)/CEP 6 | % gain | RREB1 (6p25) | % gain | | |
| BRAF (7q34) | r-gain | RREB1 (6p25) | r-gain | TK1 (17q25) | % gain | CCND (11q13) | |
| 20q13 | r-gain | RREB1 (6p25) | r-gain | TK1 (17q25) | % gain | CCND (11q13) | |

TABLE 6-continued

| | | | | | | |
|---|---|---|---|---|---|---|
| TK1/CEP10 | r-gain | BRAF (7q34) | r-gain | RREB1 (6p25) | r-gain or % abnormal | |
| TK1/CEP10 | r-gain | 20q13 | r-gain | RREB1 (6p25) | r-gain or % abnormal | |
| BRAF (7q34) | r-gain | 20q13 | r-gain | RREB1 (6p25) | r-gain | TK1 (17q25) |
| BRAF (7q34) | r-gain | RREB1 (6p25) | % gain | TK1 (17q25) | % gain | CEP10 |
| 20q13 | r-gain | RREB1 (6p25) | % gain | TK1 (17q25) | % gain | CEP10 |
| CCND/CEP10 | % gain | MYB(6q23) | r-gain | RREB1 (6p25) | % gain | |
| TK1 (17q25) | r-gain or % gain | BRAF (7q34) | r-gain | MYB(6q23)/CEP | % gain | |
| BRAF (7q34) | r-gain | CEP10 | % loss (no signals) | RREB1 (6p25) | r-gain | TK1 (17q25) |
| 20q13 | r-gain | CEP10 | % loss (no signals) | RREB1 (6p25) | r-gain | TK1 (17q25) |
| CEP10 | % loss (no signal) | RREB1 (6p25) | r-gain | COX2 (1q31) | r-gain | TK1 (17q25) |
| BRAF (7q34) | r-gain | RREB1 (6p25) | r-gain | CEP10 | % abnormal | TK1 (17q25) |
| 20q13 | r-gain | RREB1 (6p25) | r-gain | CEP10 | % abnormal | TK1 (17q25) |
| MYB(6q23) | % gain | RREB1 (6p25) | r-gain | CEP10 | % abnormal | TK1 (17q25) |
| CCND/CEP10 any del | r-gain | RREB1 (6p25) | % abnormal or % gain | TK1 (17q25) | % gain | |
| MYB(6q23) | r-gain | CEP10 | % abnormal | RREB1 (6p25) | % gain | COX2 (1q31) |
| MYB(6q23)/CEP 6 | % gain | MYB(6q23) | r-gain | RREB1 (6p25) | r-gain | CCND (11q13) |
| MYB(6q23)/CEP 6 | % gain | RREB1 (6p25) | r-gain or % abnormal | CCND (11q13) | % gain. | |
| MYB(6q23) | r-gain | RREB1 (6p25) | r-gain | COX2 (1q31) | r-gain | CEP10 |
| COX2/CEP10 | r-gain | CCND/CEP10 | r-gain | CEP10 | % loss (no signals) | RREB1 (6p25) |

| PROBE 1 | Probe 4 Parameter | # Probes | # nevi specimens | # melanoma specimens | SENS | SPEC vs norm | DFI vs norm |
|---|---|---|---|---|---|---|---|
| RREB1 (6p25) | | 1 | 30 | 33 | 0.7273 | 0.9000 | 0.2905 |
| RREB1 (6p25) | | 1 | 30 | 33 | 0.7879 | 0.8000 | 0.2915 |
| RREB1 (6p25) | | 1 | 30 | 33 | 0.7273 | 0.8667 | 0.3036 |
| COX2 (1q31) | | 1 | 30 | 33 | 0.7300 | 0.8333 | 0.3145 |
| BRAF (7q34) | | 1 | 81 | 93 | 0.6452 | 0.7160 | 0.4545 |
| 20q13 | | 1 | 81 | 94 | 0.6809 | 0.6667 | 0.4615 |
| RREB1 (6p25) | | 2 | 30 | 33 | 0.8485 | 0.8700 | 0.1966 |
| MYB(6q23) | | 2 | 30 | 33 | 0.8485 | 0.8700 | 0.1996 |
| CEP10 | | 2 | 30 | 33 | 0.8182 | 0.8700 | 0.2235 |
| RREB1 (6p25) | | 2 | 30 | 33 | 0.7576 | 0.9000 | 0.2622 |
| CEP10 | | 2 | 30 | 33 | 0.7879 | 0.8000 | 0.2915 |
| MYB(6q23) | | 2 | 30 | 33 | 0.7273 | 0.8667 | 0.3036 |
| 20q13 | | 2 | 81 | 94 | 0.7766 | 0.7778 | 0.3151 |
| RREB1 (6p25) | | 2 | 30 | 33 | 0.7273 | 0.8333 | 0.3196 |
| CEP10 | | 2 | 30 | 33 | 0.8182 | 0.7333 | 0.3228 |
| RREB1 (6p25) | | 2 | 30 | 33 | 0.8788 | 0.7000 | 0.3236 |
| COX2 (1q31) | | 2 | 30 | 33 | 0.8182 | 0.7000 | 0.3508 |
| MYB(6q23) | | 2 | 30 | 33 | 0.7273 | 0.7667 | 0.3589 |
| BRAF (7q34) | | 2 | 81 | 93 | 0.7312 | 0.7407 | 0.3735 |
| MYB(6q23) | | 2 | 30 | 33 | 0.6970 | 0.7667 | 0.3825 |
| MYB(6q23)/CEP 6 | | 3 | 30 | 33 | 0.8500 | 0.9333 | 0.1669 |
| MYB(6q23)/CEP 6 | | 3 | 30 | 33 | 0.8182 | 0.9333 | 0.1937 |
| BRAF (7q34) | | 3 | 30 | 33 | 0.8182 | 0.9333 | 0.1937 |
| 20q13 | | 3 | 30 | 33 | 0.8182 | 0.9333 | 0.1937 |
| RREB1 (6p25) | | 3 | 30 | 30 | 0.8333 | 0.9000 | 0.1944 |
| MYB(6q23)/CEP 6 | | 3 | 30 | 33 | 0.8200 | 0.9000 | 0.2075 |
| 20q13 | | 3 | 30 | 33 | 0.7879 | 0.9000 | 0.2345 |
| CCND (11q13)/CEP10 | | 3 | 30 | 33 | 0.7900 | 0.8700 | 0.2488 |
| CEP10 | | 3 | 30 | 33 | 0.7879 | 0.8667 | 0.2505 |
| 20q13 | | 3 | 30 | 33 | 0.7576 | 0.9333 | 0.2514 |
| BRAF (7q34) | | 3 | 30 | 33 | 0.7576 | 0.9333 | 0.2514 |
| 20q13 | | 3 | 30 | 33 | 0.7576 | 0.9333 | 0.2514 |
| RREB1 (6p25) | | 3 | 30 | 33 | 0.7576 | 0.9333 | 0.2514 |
| RREB1 (6p25) | | 3 | 30 | 30 | 0.8333 | 0.8000 | 0.2603 |
| RREB1 (6p25) | | 3 | 30 | 30 | 0.8333 | 0.8000 | 0.2603 |
| CCND/CEP10 any del | | 4 | 30 | 33 | 0.7576 | 0.9000 | 0.2622 |
| BRAF (7q34) | | 4 | 30 | 33 | 0.7576 | 0.9000 | 0.2622 |
| 20q13 | | 4 | 30 | 33 | 0.7576 | 0.9000 | 0.2622 |
| CEP10 | | 3 | 30 | 33 | 0.7576 | 0.9000 | 0.2622 |
| COX2 (1q31) | | 3 | 30 | 33 | 0.7576 | 0.9000 | 0.2622 |
| CEP10 | | 3 | 30 | 33 | 0.7576 | 0.9000 | 0.2622 |
| RREB1 (6p25) | | 3 | 30 | 33 | 0.7576 | 0.9000 | 0.2622 |
| RREB1 (6p25) | % gain | 3 | 30 | 33 | 0.7576 | 0.9000 | 0.2622 |
| COX2/CEP10 | | 3 | 30 | 33 | 0.7879 | 0.8333 | 0.2698 |
| CCND/CEP10 | | 3 | 30 | 33 | 0.7576 | 0.9000 | 0.2622 |
| COX2 (1q31) | | 3 | 30 | 30 | 0.8000 | 0.8000 | 0.2828 |
| RREB1 (6p25) | | 3 | 30 | 30 | 0.7667 | 0.8333 | 0.2867 |

TABLE 6-continued

| | | | | | | | |
|---|---|---|---|---|---|---|---|
| CEP10 | | 3 | 30 | 33 | 0.7273 | 0.8667 | 0.3036 |
| MYB(6q23) | | 3 | 30 | 33 | 0.7273 | 0.8667 | 0.3036 |
| COX2 (1q23) | | 3 | 30 | 33 | 0.7273 | 0.8667 | 0.3036 |
| CEP10 | | 3 | 30 | 33 | 0.7273 | 0.8667 | 0.3036 |
| 20q13 | | 3 | 81 | 93 | 0.6989 | 0.8148 | 0.3535 |
| MYB(6q23)/CEP 6 | | 4 | 30 | 33 | 0.9091 | 0.9333 | 0.1127 |
| MYB(6q23)/CEP 6 | | 4 | 30 | 33 | 0.8788 | 0.9667 | 0.1257 |
| MYB(6q23)/CEP 6 | % gain | 4 | 30 | 33 | 0.8788 | 0.9667 | 0.1257 |
| MYB(6q23)/CEP 6 | | 4 | 30 | 33 | 0.8788 | 0.9000 | 0.1571 |
| MYB(6q23)/CEP 6 | | 4 | 30 | 33 | 0.8788 | 0.9000 | 0.1571 |
| 20q13 | | 4 | 30 | 33 | 0.8485 | 0.9333 | 0.1655 |
| BRAF (7q34) | | 4 | 30 | 33 | 0.8485 | 0.9000 | 0.1815 |
| BRAF (7q34) | % gain | 4 | 30 | 33 | 0.8182 | 0.9333 | 0.1937 |
| 20q13 | % gain | 4 | 30 | 33 | 0.8182 | 0.9333 | 0.1937 |
| RREB1 (6p25) | % gain | 4 | 30 | 30 | 0.8333 | 0.9000 | 0.1944 |
| 20q13 | % gain | 4 | 30 | 33 | 0.8182 | 0.9000 | 0.2075 |
| RREB1 (6p25) | % gain | 4 | 30 | 30 | 0.8333 | 0.8667 | 0.2134 |
| BRAF (7q34) | % gain | 4 | 30 | 33 | 0.7879 | 0.9667 | 0.2147 |
| 20q13 | % gain | 4 | 30 | 33 | 0.7879 | 0.9667 | 0.2147 |
| CCND/CEP10 | | 4 | 30 | 33 | 0.7879 | 0.9333 | 0.2224 |
| CCND/CEP10 | | 4 | 30 | 33 | 0.7879 | 0.9333 | 0.2224 |
| BRAF (7q34) | % gain | 4 | 30 | 33 | 0.7879 | 0.9333 | 0.2224 |
| BRAF (7q34) | | 4 | 30 | 33 | 0.7879 | 0.9000 | 0.2345 |
| 20q13 | | 4 | 30 | 33 | 0.7879 | 0.9000 | 0.2345 |
| BRAF (7q34) | % gain | 4 | 30 | 33 | 0.7879 | 0.9000 | 0.2345 |
| 20q13 | % gain | 4 | 30 | 33 | 0.7879 | 0.9000 | 0.2345 |
| TK1/CEP10 | | 4 | 30 | 33 | 0.7576 | 0.9667 | 0.2447 |
| TK1/CEP10 | | 4 | 30 | 33 | 0.7576 | 0.9667 | 0.2447 |
| BRAF (7q34) | % gain | 4 | 30 | 33 | 0.7576 | 0.9667 | 0.2447 |
| BRAF (7q34) | % gain | 4 | 30 | 33 | 0.7879 | 0.8667 | 0.2505 |
| 20q13 | % gain | 4 | 30 | 33 | 0.7879 | 0.8667 | 0.2505 |
| CCND/CEP10 | | 4 | 30 | 33 | 0.7879 | 0.8667 | 0.2505 |
| TK1 (17q25) | | 4 | 30 | 33 | 0.7576 | 0.9333 | 0.2514 |
| BRAF (7q34) | % gain | 4 | 30 | 33 | 0.7576 | 0.9333 | 0.2514 |
| 20q13 | % gain | 4 | 30 | 33 | 0.7576 | 0.9333 | 0.2514 |
| CEP10 | % gain | 4 | 30 | 33 | 0.7576 | 0.9333 | 0.2514 |
| BRAF (7q34) | % gain | 4 | 30 | 33 | 0.7576 | 0.9333 | 0.2514 |
| 20q13 | % gain | 4 | 30 | 33 | 0.7576 | 0.9333 | 0.2514 |
| MYB(6q23) | % gain | 4 | 30 | 33 | 0.7576 | 0.9333 | 0.2514 |
| CCND/CEP10 any del | | 4 | 30 | 33 | 0.7576 | 0.9333 | 0.2514 |
| MYB(6q23) | % gain | 4 | 30 | 33 | 0.7576 | 0.9333 | 0.2514 |
| MYB(6q23)/CEP 6 | % gain | 4 | 30 | 33 | 0.7576 | 0.9333 | 0.2514 |
| MYB(6q23)/CEP 6 | | 4 | 30 | 33 | 0.7576 | 0.9333 | 0.2514 |
| MYB(6q23) | % abnormal (0 or >2 signals) | 4 | 30 | 33 | 0.7576 | 0.9000 | 0.2622 |
| COX2/CEP10 | r-gain | 4 | 30 | 33 | 0.7576 | 0.9000 | 0.2622 |

TABLE I

| PROBE 1 | PROBE 2 | PROBE 3 | PROBE 4 | IMBALANCE SENS | DFI | LOSS SENS | DFI | GAIN SENS | DFI | AMPL SENS | DFI |
|---|---|---|---|---|---|---|---|---|---|---|---|
| 09p22 | | | | 0.59 | 0.41 | 0.59 | 0.41 | 0.00 | 1.00 | 0.00 | 1.00 |
| 10q26.3 | | | | 0.36 | 0.64 | 0.35 | 0.65 | 0.01 | 0.99 | 0.00 | 1.00 |
| 06p25 | | | | 0.35 | 0.65 | 0.00 | 1.00 | 0.33 | 0.67 | 0.02 | 0.98 |
| 09q21.2 | | | | 0.35 | 0.65 | 0.34 | 0.66 | 0.01 | 0.99 | 0.00 | 1.00 |
| 01q22 | | | | 0.32 | 0.68 | 0.00 | 1.00 | 0.32 | 0.68 | 0.00 | 1.00 |
| 07p21 | | | | 0.32 | 0.68 | 0.01 | 0.99 | 0.31 | 0.69 | 0.01 | 0.99 |
| 07q36 | | | | 0.32 | 0.68 | 0.01 | 0.99 | 0.29 | 0.71 | 0.01 | 0.99 |
| 10p15 | | | | 0.28 | 0.72 | 0.28 | 0.72 | 0.00 | 1.00 | 0.00 | 1.00 |
| 08p23.2 | | | | 0.27 | 0.73 | 0.18 | 0.82 | 0.10 | 0.90 | 0.00 | 1.00 |
| 06q25.3 | | | | 0.26 | 0.74 | 0.25 | 0.75 | 0.01 | 0.99 | 0.00 | 1.00 |
| 17q25 | 09p22 | | | 0.72 | 0.28 | | | | | | |
| 09p22 | 06p25 | | | 0.70 | 0.30 | | | | | | |
| 09p22 | 06q25.3 | | | 0.69 | 0.31 | | | | | | |
| 09p22 | 01q22 | | | 0.69 | 0.31 | | | | | | |
| 09p22 | 08p23.2 | | | 0.68 | 0.32 | | | | | | |
| 09p22 | 07p21 | | | 0.68 | 0.32 | | | | | | |
| 10q26.3 | 09p22 | | | 0.68 | 0.32 | | | | | | |
| 09p22 | 07q36 | | | 0.68 | 0.32 | | | | | | |
| 09p22 | 08q24.2 | | | 0.68 | 0.32 | | | | | | |
| 20q13.3 | 09p22 | | | 0.66 | 0.34 | | | | | | |
| 17q25 | 09p22 | 06p25 | | 0.79 | 0.21 | | | | | | |
| 17q25 | 09p22 | 08p23.2 | | 0.78 | 0.22 | | | | | | |
| 17q25 | 10q26.3 | 09p22 | | 0.77 | 0.23 | | | | | | |
| 17q25 | 09p22 | 08q24.2 | | 0.77 | 0.23 | | | | | | |

TABLE I-continued

| PROBE 1 | PROBE 2 | PROBE 3 | PROBE 4 | IMBALANCE SENS | DFI | LOSS SENS | DFI | GAIN SENS | DFI | AMPL SENS | DFI |
|---|---|---|---|---|---|---|---|---|---|---|---|
| 20q13.3 | 17q25 | 09p22 | | 0.77 | 0.23 | | | | | | |
| 09p22 | 08p23.2 | 06q25.3 | | 0.76 | 0.24 | | | | | | |
| 09p22 | 08p23.2 | 06p25 | | 0.76 | 0.24 | | | | | | |
| 09p22 | 07p21 | 06p25 | | 0.76 | 0.24 | | | | | | |
| 09p22 | 06p25 | 01q22 | | 0.76 | 0.24 | | | | | | |
| 17q25 | 09p22 | 06q25.3 | | 0.76 | 0.24 | | | | | | |
| 10cen | 17q25 | 09p22 | 06p25 | 0.82 | 0.18 | | | | | | |
| 17q25 | 10q26.3 | 09p22 | 06p25 | 0.82 | 0.18 | | | | | | |
| 17q25 | 09p22 | 08p23.2 | 06p25 | 0.82 | 0.18 | | | | | | |
| 20q13.3 | 17q25 | 09p22 | 08p23.2 | 0.82 | 0.18 | | | | | | |
| 01cen | 09p22 | 06q25.3 | 06p25 | 0.82 | 0.18 | | | | | | |
| 06cen | 17q25 | 10q26.3 | 09p22 | 0.82 | 0.18 | | | | | | |
| 06cen | 17q25 | 09p22 | 08p23.2 | 0.82 | 0.18 | | | | | | |
| 06cen | 09p22 | 08p23.2 | 01q22 | 0.82 | 0.18 | | | | | | |
| 08cen | 17q25 | 09p22 | 06p25 | 0.82 | 0.18 | | | | | | |
| 10cen | 06cen | 17q25 | 09p22 | 0.82 | 0.18 | | | | | | |

What is claimed is:

1. A hybridization method comprising:
a) contacting a sample of a skin lesion from a human subject with a combination consisting of four detectably labeled in situ hybridization probes, the four detectably labeled in situ hybridization probes consisting of a probe that selectively hybridizes to a target sequence within chromosome subregion 6p25, a probe that selectively hybridizes to a target sequence within chromosome subregion 6q23, a chromosome 6 enumerator probe that comprises a repetitive DNA sequence and selectively hybridizes to the centromeric or peri-centromeric region of chromosome 6, and an additional probe,
wherein the additional probe is selected from the group consisting of a chromosome 10 enumerator probe that comprises a repetitive DNA sequence and selectively hybridizes to the centromeric or peri-centromeric region of chromosome 10, a probe that selectively hybridizes to a target sequence within chromosome subregion 7q34, a probe that selectively hybridizes to a target sequence within chromosome subregion 11q13, a probe that selectively hybridizes to a target sequence within chromosome subregion 17q25, and a probe that selectively hybridizes to a target sequence within chromosome subregion 20q13; and
wherein the target sequence for each probe is from 70,000 nucleotides to 800,000 nucleotides, and each probe hybridizes along the entire length of its target sequence;
b) incubating each probe of the combination with the skin lesion sample under in situ hybridization conditions in which each probe selectively hybridizes to its target sequence to form a stable hybridization complex, wherein each probe hybridizes to a lesser extent to, or not at all to non-target sequences, as compared to target sequences; and
c) detecting hybridization of the combination of probes to determine copy number at any chromosome subregion to which the probes selectively hybridize,
wherein the hybridization method employs no additional in situ hybridization probes beyond those in the combination.

2. The method of claim 1, wherein the skin lesion sample is a formalin-fixed, paraffin-embedded sample.

3. The method of claim 1, wherein the detectable label is a fluorescent label.

4. The method of claim 1, wherein the additional probe is said chromosome 10 enumerator probe that comprises a repetitive DNA sequence and selectively hybridizes to the centromeric or peri-centromeric region of chromosome 10.

5. The method of claim 1, wherein the additional probe is said probe that selectively hybridizes to a target sequence within chromosome subregion 7q34.

6. The method of claim 1, wherein the additional probe is said probe that selectively hybridizes to said target sequence within chromosome subregion 11q13.

7. The method of claim 1, wherein the additional probe is said probe that selectively hybridizes to said target sequence within chromosome subregion 17q25.

8. The method of claim 1, wherein the additional probe is said probe that selectively hybridizes to a target sequence within chromosome subregion 20q13.

9. The method of claim 1, wherein the target sequence for each probe is at least 100,000 nucleotides.

* * * * *